US006407060B1

(12) United States Patent
Charette et al.

(10) Patent No.: US 6,407,060 B1
(45) Date of Patent: *Jun. 18, 2002

(54) METHOD FOR ENHANCING FUNCTIONAL RECOVERY FOLLOWING CENTRAL NERVOUS SYSTEM ISCHEMIA OR TRAUMA

(75) Inventors: Marc F. Charette; Seth P. Finklestein, both of Needham, MA (US)

(73) Assignee: Curis, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/828,281

(22) Filed: Mar. 21, 1997

Related U.S. Application Data

(63) Continuation-in-part of application No. 08/620,444, filed on Mar. 22, 1996, now abandoned.

(51) Int. Cl.⁷ ............................................... A61K 38/00
(52) U.S. Cl. ........................... 514/12; 514/21; 530/324; 530/350
(58) Field of Search ..................... 514/12, 21; 530/324, 530/350

(56) References Cited

U.S. PATENT DOCUMENTS

| | | | |
|---|---|---|---|
| 4,440,860 A | 4/1984 | Klagsbrun | 435/240 |
| 4,465,669 A | 8/1984 | Wissler et al. | 424/177 |
| 4,797,277 A | 1/1989 | Arfors | 424/85.8 |
| 4,801,575 A | 1/1989 | Pardridge | 514/4 |
| 4,806,523 A | 2/1989 | Bentz et al. | 514/2 |
| 4,861,757 A | 8/1989 | Antoniades et al. | 514/21 |
| 4,952,409 A | 8/1990 | Bando et al. | 424/450 |
| 4,971,952 A | 11/1990 | Bentz et al. | 514/2 |
| 4,983,581 A | 1/1991 | Antoniades et al. | 514/12 |
| 5,002,965 A | 3/1991 | Ramwell et al. | 514/468 |
| 5,008,240 A | 4/1991 | Bentz et al. | 514/2 |
| 5,008,246 A | 4/1991 | Schon et al. | 514/18 |
| 5,011,691 A | 4/1991 | Oppermann et al. | 424/423 |
| 5,108,753 A | 4/1992 | Kuberasamphath et al. | 424/422 |
| 5,108,989 A | 4/1992 | Amento et al. | 514/12 |
| 5,118,791 A | 6/1992 | Burnier et al. | 530/326 |
| 5,135,915 A | 8/1992 | Czarniecki et al. | 514/21 |
| 5,158,934 A | 10/1992 | Ammann et al. | 514/12 |
| 5,393,739 A | 2/1995 | Bentz et al. | 514/12 |
| 5,462,925 A | 10/1995 | Ogawa et al. | 514/12 |

FOREIGN PATENT DOCUMENTS

| | | |
|---|---|---|
| EP | 0269408 | 1/1988 |
| EP | 0512844 | 11/1992 |
| EP | 0514720 | 11/1992 |
| WO | WO 84/01106 | 3/1984 |
| WO | WO 88/00205 | 1/1988 |
| WO | WO 90/00619 | 1/1990 |
| WO | WO 90/00900 | 2/1990 |
| WO | WO 90/03733 | 4/1990 |
| WO | WO 91/05802 | 5/1991 |
| WO | WO 92/00382 | 1/1992 |
| WO | WO 92/05199 | 4/1992 |
| WO | WO 92/07073 | 4/1992 |
| WO | WO 92/09301 | 6/1992 |
| WO | WO 92/09697 | 6/1992 |
| WO | WO 92/15323 | 9/1992 |
| WO | WO 92/20371 | 11/1992 |
| WO | WO 92/20793 | 11/1992 |
| WO | WO 93/00050 | 1/1993 |
| WO | WO 93/00432 | 1/1993 |
| WO | 9304692 | * 3/1993 |
| WO | WO 93/04692 | 3/1993 |
| WO | 9308828 | * 5/1993 |
| WO | WO 93/09229 | 5/1993 |
| WO | 9309802 | * 5/1993 |
| WO | WO 94/03200 | 2/1994 |
| WO | WO 95/05846 | 3/1995 |
| WO | WO 95/06656 | 3/1995 |
| WO | WO95/10611 | 4/1995 |
| WO | WO 95/24474 | 9/1995 |

OTHER PUBLICATIONS

Perides et al., *Neuroscience Letters*, vol. 187, No. 1, pp. 21–24, Feb. 24, 1995.*

Aebischer et al. (1989), "Basic Fibroblast Growth Factor Released From Synthetic Guidance Channels Facilitating Peripheral Nerve Regeneration Across Long Nerve Gaps," 23 *J. Neurosci. Res.* 282–289.

Attisano et al. (1992), "Novel Activin Receptors Distinct Genes and Alternative mRNA Splicing Generate A Repertoire of Serine Threonine Kinase Receptors", 68 *Cell* 97–108.

Audus et al. (1987), "Bovine Brain Microvessel Endothelial Cell Monolayers As A Model System For The Blood–Brain Barrier," 507 *Ann. N.Y. Acad. Sci.* 9–18.

Barde (1989), "Trophic Factors And Neuronal Survival," 2 *Neuron* 1525–1534.

Basler et al., (1993) "Control of Cell Pattern in the Neural Tube: Regulation of Cell Differentiation by dorsalin– 1, a Novel TGFβ Family Member", 73 *Cell,* 68–702.

(List continued on next page.)

*Primary Examiner*—Raymond Henley, III
*Assistant Examiner*—C. Delacroix-Muirheid
(74) *Attorney, Agent, or Firm*—Ropes & Gray

(57) ABSTRACT

The present invention provides methods and compositions for treatment of mammals afflicted with an ischemic or traumatic injury of the central nervous system. The present invention capitalizes in part upon the discovery that administration of a morphogen to such a mammal provides significant improvement in central nervous system function, even when administered after central nervous system tissue has been damaged. The methods involve the administration of dimeric proteins defined as morphogens, inducers of these morphogens, or agonists of the corresponding morphogen receptors, or implantation of cells stimulated by exposure to the morphogens. The proteins defined as morphogens comprise a structurally and functionally distinct family within the TGF-β superfamily. Osteogenic protein-1 (OP-1) is considered to be an exemplary and preferred member of this morphogen family.

30 Claims, 14 Drawing Sheets

OTHER PUBLICATIONS

Beck et al. (1990), "Accelerated Healing of Ulcer Wounds In The Rabbit Ear By Recombinant Human Transforming Growth Beta 1," 2 *Growth Factors* 273–282.

Bhat (1988), "NCAM–1 80, The Largest Component Of The Neural Cell Adhesion Molecule, Is Reduced In Dysmyelmatmg Quaking Mutant Mouse Brain," 452 *Brain Res* 373–377.

Bignami et al. (1974), "Astrocyte–Specific Protein and Neuroglial Differentiation: An Immunofluorescence Study With Antibodies to the Glial Fibrillary Acidic Protein," 153 *J. Comp. Neur.* 27–38.

Birren et al. (1993), "Sympathetic Neuroblasts Undergo a Developmental Switch In Trophic Dependence," 119 *Develop.* 597–610.

Bitgood et al. (1995), "Hedgehog and Bmp Genes are Coexpressed at Many Diverse Sites of Cell–Cell Interaction in the Mouse Embryo" 172 *Dev. Biol.* 126–138.

Border et al., (1992) "Transforming Growth Factor–B in Disease: The Dark Side of Tissue Repair", *J. Clin. Invest,* 90:1–7.

Brackenbury (1988), "Expression of Neural Cell Adhesion Molecules In Normal and Pathologic Tissue," 540 *Annals. N.Y. Acad. Sci.* 39–46.

Bradshaw et al. (1993), "Nerve Growth Factor Revisited," 18 *TIBS.*

Bruckenstein et al. (1988), "Morphological Differentiation of Embryonic Rat Sympathetic Neurons in Tissue Culture," 128 *Dev. Biol.* 324–336.

Brunner et al. (1989), 254 *J. Biol. Chem.* 13660.

Buskirk et al. (1980), "Antibodies to Neural Cell Adhesion Molecule Disrupt Histogenesis In Cultured Chick Retinae," 285 *Nature* 5765:488–489.

Carswell (1993), "The Potential for Treating Neurodegenerative Disorders with NGF–Inducing Compounds," 124 *Exp. Neurol.* 36.

Clendening et al. (1990), "Cell Interactions Regulate Dendritic Morphology and Responses to Neurotransmitters in Embryonic Chick Sympathetic Preganglionic Neurons In Vitro," 10 1 *Neurosci.* 5:3992–4005.

Crossin (1991), "Cell Adhesion Molecules In Embryogenesis and Disease," 615 *Annals. N.Y. Acad. Sci.* 172–186.

Cunningham et al. (1987), "Neural Cell Adhesion Molecule: Structure, Immunoglobulin–Like Domains, Cell Surface Modulation, and Alternative RNA Splicing," 236 *Science* 799–806.

de Koninck et al. (1993), "NGF Induced Neonatal Rat Sensory Neurons to Extend Dendrites in Culture After Removal of Satellite Cells," 13 *J. Neurosci* 577–5 85.

Dedhar et al. (1993), "Differential Regulation of Expression of Specific Integrin Receptors By Nerve Growth Factor and Transforming Growth Factor 31 During Differentiation of Human Neuroblastoma Cells," 1 *Mol. Cell Diff.* 1–20.

Deininger et al. (1995), "Detection of Two Transforming Growth Factor–13–Related Morphogens, Bone Morphogenetic Proteins –4 and –5, in RNA of Multiple Sclerosis and Creutzfeldt–Jakob Disease Lesions," 90 *Acta Neuropathol.* 76–79.

Dotti et al. (1988), "The Establishment of Polarity in Hippocampal Neurons in Culture," 8 *J. Neurosci.* 1454–1468.

Ebendal (1992), "Function and Evolution in the NGF Family and Its Receptors," 32 *J. Neurosci. Res.* 461.

Ebendal et al. (1991) "Human Nerve Growth Factor: Biological and Immunological Activities, and Clinical Possibilities in the Neurodegenerative Disease," Plasticity and Regeneration of the Nervous System 207–225 (Timeras et al. , eds., Plenum Press N.Y.).

Edelman (1985), "Cell Adhesion and The Molecular Processes of Morphogenesis," 54 *Ann. Rev. Biochem.* 135–169.

Edelman (1986), "Cell Adhesion Molecules in the Regulation of Animal Form and Tissue Pattern," 2 *Ann Rev. Cell. Biol.* 81–116q.

Friedlander et al. (1986), "Nerve Growth Factor Enhances Expression of Neuron–Glia Cell Adhesion Molecules in PC12 Cells," 102 *J.C.B.* 413–419.

Gash et al. (1996), "Functional Recovery in Parkinsonian Monkeys Treated with GDNF", 380 *Nature* 252–255.

Green et al. (1990), "Graded Changes in Dose of a Xenopus Activin A Homologue Elicit Stepwise Transitions in Embryonic Cell Fate," *Nature* 347:391–394.

Gross et al. (1993), "Transforming Growth Factor–$\beta$1 Reduces Infarct Size After Experimental Cerebral Ischemia in a Rabbit Model," 24 *Stroke* 558–562.

Hammond et al. (1985), "Oxygen Radicals In The Adult Respiratory Distress Syndrome, In Myocardial Ischemia And Reperfusion Injury, And In Cerebral Vascular Damage," 63 *Can J. Physiol. Pharmacol.* 173–187.

Hefti et al. (1993), "Pharmacology of Nerve Growth Factor in the Brain," 24 *Adv. in Pharmacol.* 239–273.

Hogan, Bridig L.M. (1995), "Upside–Down Ideas Vindicated," 376 *Nature* 210–211.

Jackowski et al. (1995), "Neural Injury Repair: Hope For The Future As Barrier To Effective CNS Regeneration Become Clearer," 9 *Brit. J. Neurosurgery,* 303–317.

Johnson et al. (1989), "Astrocytes Induced Dendritic Development in Cultured Sympathetic Neurons," 47 *Dev. Brain Res.* 289–292.

Jones et al. (1991), "Involvement of Bone Morphogenetic Protein–4 (BMP–4) and Vgr–1 in Morphogenesis and Neurogenesis in the Mouse," 111 *Development* 2: 531–542.

Jones et al. (1991), "Involvement of Bone Morphogenetic Proteins," 91 *Biol. Abstracts* 10:AB–444, No. 106862.

Kingsley, (1994) "The TGF–$\beta$ superfamily: new members, new receptors, and new genetic tests of function in different organisms", *Genes and Development,* 8:133–146.

Kondo et al. (1991), "Activin Receptor mRNA is Expressed Early in Xenopus Embryogenesis and the Level of the Expression Affects the Body Axis Formation", 181 *Biochem. & Biophys. Res. Comm.* 2:684–690.

Krummel et al., (1988) "Transforming Growth Factor Beta (TGF–13) Induces Fibrosis in a Fetal Wound Model", *Journal of Pediatric Surgery,* 23 :647–652.

Lee (1990), "Identification of a Novel Member (GDF–1) of the Transforming Growth Factor–B Superfamily," *Molecular Endocrinology* 4 (No. 7):1034–1040.

Lee (1991), "Expression of Growth/Differentiation Factor 1 in the Nervous System: Conservation of a Bicistronic Structure," 88 *Proc. Natl. Acad. Sci. USA,* 4250–4254.

Lefer et al. (1992), "Anti–Ischaemic and Endothelial Protective Actions of Recombinant Human Osteogenic Protein (hOP–1)," *J. Mol. Cell. Card.* 24: 585–593.

Lefer et al. (1990), "Mediation of Cardioprotection by Transforming Growth Factor–$\beta$," *Science* 249: 61–64.

Leibowitz, et al. (1990), "Effect of Topically Administered Epidermal Growth Factor on Corneal ound Strength," *Arch. Ophthalmol.,* 108: 734–737.

Lein et al. (1996), "The Effects of Extracellular Matrix and Osteogenic Protein–I On The Morphological Differentiation of Rat Sympathetic Neurons," 14 *Int. J. Devl. Neurosci.* 3: 203–215.

Leim et al. (1995), "Dorsal Differentiation of Neural Plate Cells Induced by BMP–Mediated Signals from Epidermal Ectoderm," 82 *Cell* 969–979.

Lein et al. (1995), "Osteogenic Protein–1 Induced Dendritic Growth in Rat Sympathetic Neurons," 15 *Neuron* 597–605.

Lein et al. (1989), "Laminin and a Basement Membrane Extract Have Different Effects on Axonal and Dendritic Outgrowth From Embryonic Rat Sympathetic Neurons In Vitro" 136 *Dev. Biol.* 330–345.

LeRoux et al. (1994), "Regional Differences in Glial Derived Factors That Promote Dendritic Outgrowth From Mouse Cortical Neurons In Vitro," 14 *J. Neurosci.* 8: 4639–4655.

Letsou et al. (1995), "Drosophila Dpp Signaling Is Mediated By The Punt Gene Product: A Dual Ligand–Binding Type II Receptor Of The TGF–$\beta$ Receptor Family," 80 *Cell* 899–908.

Linnemann et al. (1989), "Cell Adhesion Molecules in Neural Development," 11 *Dev. Neurosci.* 149–173.

Lorant et al. (1991), "Coexpression of GMP–140 and PAF by Endothelium Stimulated by Histamine or Thrombin: A Juxtacrine System For Adhesion and Activation of Neutrophils," 115 *J.C.B.* 223–234.

Lundborg (1987), "Nerve Regeneration and Repair," 58 *Acta. Orthop. Scand.* 145–169.

Lyons et al. (1988), "The Expression of an N–CAM Serum Fragment Is Positively Correlated With Severity of Negative Features in Type II Schizophrenia," 23 *Biol. Psychiatry* 769–775.

Lyons et al. (1990), "Transforming Growth Factors and the Regulation of Cell Proliferation," 187 *Eur. J. Biochem.* 467–473.

Mahony et al. (1995), "A type 1 serine/threonine kinase receptor that can dorsalize mesoderm in Xenopus" 92 *Proc. Natl. Acad Sci. USA* 6474–6478.

Mann et al. (1989), "Increased Intracellular Cyclic AMP Differentially Modulates Nerve Growth Factor Induction Of Three Neuronal Recognition Molecules Involved In Neurite Outgrowth," 53 *J. Neurochem.* 1581–1588.

Massague (1990), "The Transforming Growth Factor–B Family," *Ann. Rev. Cell Biol.* 6:597–641.

Massague (1992), "Receptors for the TGF–B Family", 69 *Cell* 1067–1070.

Massague, J. (1996) "TGF$\beta$ Signaling: Receptors, Transducers, and Mad Proteins," 85 *Cell* 947–950.

Miyazono et al. (1993), "Transforming Growth Factor–$\beta$: Latent Foims, Binding Proteins and Receptors," 8 *Growth Factors* 11–22.

Ogata, T. et al. (1993) "Bone morphogenetic protein–2–transiently enhanced expression of a gene, Id (inhibitor of differentiation), encoding a helix–loop–helix molecule in osteoblast–like cells," 90 *Proc. Natl. Acad Sci. USA* 9219–9222.

Ozkaynak et al. (1992), "Organ Specific Expression of Selected TGF–$\beta$ Superfamily Members," 81 *J. Cell Biochem.* Abstract W114.

Ozkaynak et al. (1992), "Osteogenic Protein–2: A New Member Of The Transforming Growth Factor–$\mu$ Superfamily Expressed In Early Embryogenesis," 267 *J. Biol. Chem.* 25220–25227.

Ozkaynak et al., (1990) "OP–I cDNA encodes an osteogenic protein in the TGF–$\beta$ family", *EMBO J.* 9:2085–2093.

Panganiban et al., (1990) "Biochemical Characterization of the Drosophila dpp Protein, a Member of the Transforming Growth Factor $\beta$ Family of Growth Factors", *Mol and Cell. Biol.* 10:2669–2677.

Paralkar et al. (1992), "Recombinant Human Bone Morphogenetic Protein Stimulates PC12 Cell Differentiation: Potentiation and Binding to Type IV Collagen," 119 *J. Cell Biol.* 172: 1–1728.

Pardridge (1986), "Receptor–Mediated Peptide Transport Through The Blood–Brain Barrier," 7 *Endocr. Rev.* 314–330.

Pardridge et al. (1987), "Chimeric Peptides As A Vehicle for Peptide Pharmaceutical Delivery Through The Blood–Brain Barrier," 146 *Biochem. Biophys. Res. Commun.* 307–313.

Perides et al. (1995), "Neuroprotective Effect of Human Osteogenic Protein 1 in a Rat Model of Cerebral Hypoxia/Ischemia," 187 *Neurosci. Lett.* 21–24.

Perides et al., (1994) "Regulation of Neural Cell Adhesion Molecule and Li by the Transforming Growth Factor–$\beta$ Superfamily", *J. Biological Chemistry*, 269:765–770.

Perides et al. (1993), "Osteogenic Protein–1 Regulated L1 and Neural Cell Adhesion Molecule Gene Expression in Neural Cells," 268 *J. Biol. Chem.* 25 197–25205.

Perides et al. (1992), "Induction of the Neural Cell Adhesion Molecule and Neuronal Aggregation by Osteogenic Protein–1," 89 *Proc. Natl. Acad. Sci. USA* 10326–10330.

Postlethwaite et al. (1976), "The Chemotactic Attraction of Human Fibroblasts to a Lymphocyte–Derived Factor," 144 *J. Exp. Med.* 1188–1203.

Purves et al. (1988), "Trophic Regulation of Nerve Cell Morphology and Innervation in the Autonomic Nervous System," 3336 *Nature* 123–128.

Reissmann et al. (1996), "Involvement of Bone Morphogenic Protein–4 and Bone Morphogenic Protein–7 In The Differentiation of the Adrenergic Phenotype In Developing Sympathetic Neurons," 122 *Development* 2079–2088.

Remsen (1990), "Antibodies to the Neural Cell Adhesion Molecule Disrupt Functional Recovery In Injured Nerves," 110 *Exp. Neurobiol.* 268–273.

Roberts et al. (1986). "Transforming Growth Factor Type–Beta: Rapid Induction of Fibrosis and Angiogenesis In Vivo and Stimulation of Collagen Formation In Vitro," 83 *Proc. Natl. Acad. Sci. USA* 4167–4171.

Rosenzweig et al. (1995), "Cloning And Characterization Of A Human Type II Receptor For Bone Morphogenic Proteins," 92 *Proc. Natl. Acad. Sci. USA* 7632–7636.

Roubin et al. (1990), "Modulation of NCAM Expression by Transforming Growth Factor–Beta, Serum, and Autocrine Factors," 111 *J. Cell Biol.* 673–684.

Ruberte et al. (1995), "An Absolute Requirement For Both The Type II and Type I Receptor, Punt And Thick Veins, For Dpp Signaling In Vivo," 80 *Cell* 889–897.

Rutihauser et al. (1988), "The Neural Cell Adhesion Molecule (NCAM) As A Regulator of Cell–Cell Interactions," 240 *Science* 53–57.

Saad et al. (1991), "Astrocyte–Derived TGF–$\beta$ and NGF Differentially Regulate Neural Recognition Molecule Expression by Cultured Astrocytes," 115 *J. Cell Biol.* 2: 473–484.

Sasai et al. (1995), Regulation of Neural Induction by the Chd and Bmp–4 Antagonistic Patterning Signals in Xenopus, 376 *Nature* 333–336.

Schluesener et al. (1995), "Immunolocalization of vgr (BMP–6, DVR–6), a TGF–β–Related Cytokine, to Schwann Cells of the Rat Peripheral Nervous System: Expression Patterns Are Not Modulated by Autoimmune Disease," 13 *GLIA* 75–78.

Schmidt et al. (1995), "Localizaed BMP–4 mediates dorsal/ventral patterning in the early Xenopus embryo," 169 *Devel. Biol.* 37–50.

Schubert et al., (1990) "Activin is a nerve cell survival molecule", *Nature* 344: 868–870.

Schultz et al., (1991) "Neovascular Growth Factors", *Eye* 5: 170–180.

Shah et al. (1995), "Alternative Neural Crest Cell Fates Are Instructively Promoted by TGF–β Superfamily Members," 85 *Cell* 331–343.

Shipley et al. (1986), "Reversible Inhibition of Normal Human Prokeratinocyte Proliferation by Type Beta Transforming Growth Factor–Growth Inhibitor In Serum–Free Media," 46 *Cancer Res.* 2068–2071.

Snider (1988), "Nerve Growth Factor Enhances Dendritic Arborization of Sympathetic Ganglion Cells in Developing Mammals," 8 *J. Neurosci.* 2628–2634.

Sporn et al. (1989), "Transforming Growth Factor–β," 262 *J. Amer. Med. Assoc.* 938–941.

Stenzel et al. (1994), "The Univin Gene Encodes A Member Of The Transforming Growth Factor–β Superfamily With Restricted Expression In The Sea Urchin Embryo," 166 *Dev. Biol.* 149–158.

Stromberg et al. (1993), "Glial Cell Line–Derived Neurotrophic Factor is Expressed in the Developing but Not Adult Striatum and Stimulates Developing Dopamine Neurons in vivo," 124 *Exp. Neurol.* 401–412.

Struhl et al. (1989), "The Gradient Morphogen bicoid as a Concentration–Dependent Transcriptional Activator," 57 *Cell* 1259–1273.

Suzuki, A. et al. (1994), "A truncated bone morphogenetic protein receptor affects dorsal–ventral patterning in the early Xenopus embryo," 91 *Proc. Natl. Acad. Sci. USA* 10255–10259.

Swindells (1992), Structural Similarity Between Transforming Growth Factor B2 and Nerve Growth Factor, 258 *Science* 1160.

Tomac et al. (1995), "Protection and Repair of the Nigrostriatal Dopaminergic System by GDNF in vivo," 373 *Nature* 335–346.

Turing (1952), "The Chemical Basis Of Morphogenesis," 237 *Phil. Trans. Roy. Soc. B.* 37–39.

Van Den Eijnden–Van Raaij et al. (1990), "Activin–Like Factor from a Xenopus Laevis Cell Line for Mesoderm Induction," *Nature* 345: 732–734.

Varley et al. (1995), "Number of Adrenergic and Islet–1 Immunoreactive Cells Is Increased In Avian Trunk Neural Crest Cultures in the Presence of Human Recombinant Osteogenic Protein–1," 203 *Dev. Dynamics* 434–447.

Varley et al. (1995), "The Effects of BMP–2, –4 and –6 on the Development of the Adrenergic Phenotype in Quail Trunk Neural Crest Cultures," 21 *Soc. Neurosci.* 1543.

Vedder et al. (1990), "Inhibition of Leukocyte Adherence by Anti–CD18 Monoclonal Antibody Attenuates Reperfusion Injury in the Rabbit Ear," 87 *Proc. Natl. Acad. Sci. USA* 2643–2646.

Wahl (1992), "Transforming Growth Factor Beta (TFG–β) in Inflammation: A Cause and A Cure," 12 *J. Clin. Immunol.* 2:–61–74.

Wahl et al. (1989), "Inflammatory and Immunomodulatory Roles of TGF–β," 10 *Immun. Today* 258–261.

Wall et al (1993), "Biosynthesis and In Vivo Localization of the Decapentaplegic–Vg–Related Protein, DVR–6 (Bone Morphogenetic Protein–6)," 120 *J. Cell Biol.* 2: 493–502.

Werdelin (1989), "Neuropeptides and Neural Cell Adhesion Molecule (NCAM) in CSF From Patients With ALS," 79 *Acta. Neurol. Scand.* 177–181.

Wharton et al. (1991), "Drosophila 60A Gene, Another Transforming Growth Factor 13 Family Member, is Closely Related to Human Bone Morphogenetic Proteins," 88 *Proc. Natl. Acad. Sci. USA,* 9214–9218.

Whitby et al., (1991),"Immunohistochemical Localization of Growth Factors in Fetal Wound Healing", *Developmental Biology,* 147:207–215.

Wilson et al. (1995), "Induction of Epidermis and Inhibition of Neural Fate by Bmp–4," 376 *Nature* 33: 1–333.

Withers et al. (1996), "Receptivity of Osteogenic Protein–I (OP–1) – Induced Dendrites to Axonal Innervation," Society for Neuroscience meeting abstract.

Withers et al. (1995), "Osteogenic Protein–1 (OP–I) Induces Dendritic Growth and Branching in Cultured Hippocampal Neurons", Society for Neuroscience meeting abstract.

Wozney (1989) "Bone Morphogenetic Proteins", *Progress in Growth Factor Research,* 1: 267–280.

Wozney et al. (1988) "Novel Regulators of Bone Formation: Molecular Clones and Activities" *Science* 242: 1528–1534.

Wozney et al. (1990) "Growth factors influencing bone development," *J. Cell Sci.* Suppl. 13: 149–156.

Yamamoto et al. (1 993),"Expression of Transforming Growth Factor β is Elevated in Human and Experimental Diabetic Nephrology," 90 *Proc. Natl. Acad. Sci. USA* 1814–1818.

Yannas, (1990) "Biologically Active Analogues of the Extracellular Matrix: Artificial Skin and Nerves," *Chem. Int. Ed. Engl.* 29: 20–35.

* cited by examiner

| % Amino Acid Sequence Similarity, Identity to Human OP-1 7-Cysteine Domain | | |
|---|---|---|
| >=70% Sequence | % Similarity | % Identity |
| hOP-1 (hBMP-7) | 100 | 100 |
| mOP-1 (mBMP-7) | 100 | 99 |
| hOP-2 (hBMP-8) | 97 | 72 |
| mOP-2 (mBMP-8) | 97 | 75 |
| hBMP-5 | 97 | 88 |
| hBMP-6 (Vgr-1) | 96 | 87 |
| Vgr-1 (PT) | 94 | 85 |
| OP-3 | 91 | 66 |
| d60A | 90 | 69 |
| BMP-4 (BMP-2b) | 90 | 58 |
| BMP-2 (BMP-2a) | 89 | 60 |
| dpp | 87 | 57 |
| sUNIVIN | 87 | 63 |
| xVg-1 | 86 | 58 |
| hCDMP-1 (mGDF-5) | 85 | 50 |
| hCDMP-3 (mGDF-7, hBMP-12) | 83 | 54 |
| mGDF-3 (hVgr-2) | 83 | 50 |
| hCDMP-2 (mGDF-6, hBMP-13) | 82 | 53 |
| cDORSALIN | 79 | 50 |
| hGDF-1 | 78 | 49 |
| mGDF-10 | 78 | 40 |
| rBMP-3b | 78 | 41 |
| hBMP-10 | 78 | 47 |
| hBMP-3 | 78 | 43 |
| dSCREW | 77 | 49 |
| ADMP | 77 | |
| mGDF-1 | 73 | 50 |
| hBMP-9 | 73 | 52 |
| mNODAL | 71 | 41 |
| hBMP-15 | 71 | 41 |

FIG. 1

METHOD FOR ENHANCING FUNCTIONAL RECOVERY FOLLOWING CENTRAL NERVOUS SYSTEM ISCHEMIA OR TRAUMA

The present application is a continuation-in-part of U.S. application Ser. No. 08/620,444 filed Mar. 22, 1996, now abandoned the disclosure of which is incorporated herein by reference.

STATEMENT REGARDING FEDERALLY SPONSORED RESEARCH

Work described herein was made with government support under Contract Number NS 10828, awarded by the National Institutes of Health. The government has certain rights in the invention.

FIELD OF THE INVENTION

The present invention generally relates to methods and compositions for the treatment of mammals, including humans, following an ischemic or traumatic injury to the central nervous system.

BACKGROUND OF THE INVENTION

Numerous proteins have now been identified and characterized as morphogenetic or growth factors, regulating cell proliferation and/or differentiation of tissues in vertebrates, including mammals. Typically these growth factors exert their effects on specific subsets of cells and/or tissues. Thus, for example, epidermal growth factors, nerve growth factors, fibroblast growth factors, various hormones, and many other proteins inducing or inhibiting cell proliferation or differentiation have been identified and shown to affect some subset of cells or tissues.

Neurotrophic factors are polypeptides that are required for the development of the nervous system. The first neurotrophic factor discovered, nerve growth factor (NGF), is now known to be a part of a large family of growth factors, which also includes BDNF, NT3, and NT4/NT5. The dimeric proteins defined in PCT Publication No. WO 94/03200 as morphogens constitute another family of proteins believed to play an important role in neural development (Jones, et al. (1991) *Development* 111: 531–542; Ozkaynak, et al. (1992) *J. Biol. Chem.* 267: 25220–25227; Lein, et al. (1995) *Neuron* 15: 597–605).

These proteins, referred to herein as "morphogenic proteins" or "morphogens," are competent to act as true tissue morphogens, able, on their own, to induce the proliferation and differentiation of progenitor cells into functional mammalian body tissue. The proteins include members of the family of bone morphogenetic proteins (BMPs) which were initially identified by their ability to induce ectopic, endochondral bone morphogenesis.

Morphogens generally are classified in the art as a subgroup of the TGF-β superfamily of growth factors (Hogan (1996) *Genes & Development* 10: 1580–1594). Members of the morphogen family of proteins include the mammalian osteogenic protein-1 (OP-1, also known as BMP-7, and the Drosophila homolog 60A), osteogenic protein-2 (OP-2, also known as BMP-8), osteogenic protein-3 (OP-3), BMP-2 (also known as BMP-2A or CBMP-2A, and the Drosophila homolog DPP), BMP-3, BMP-4 (also known as BMP-2B or CBMP-2B), BMP-5, BMP-6 and its murine homolog Vgr-1, BMP-9, BMP-10, BMP-11, BMP-12, GDF-3 (also known as Vgr2), GDF-8, GDF-9, GDF-10, GDF-11, GDF-12, BMP-13, BMP-14, BMP-15, GDF-5 (also known as CDMP-1 or MP52), GDF-6 (also known as CDMP-2), GDF-7 (also known as CDMP-3), the Xenopus homolog Vgl and NODAL, UNIVIN, SCREW, ADMP, and NEURAL. The members of this family encode secreted polypeptide chains sharing common structural features, including processing from a precursor "pro-form" to yield a mature polypeptide chain competent to dimerize, and containing a carboxy terminal active domain of approximately 97–106 amino acids. All members share a conserved pattern of cysteines in this domain and the active form of these proteins can be either a disulfide-bonded homodimer of a single family member, or a heterodimer of two different members (see, e.g., Massague (1990) *Annu. Rev. Cell Biol.* 6: 597; Sampath, et al. (1990) *J. Biol. Chem.* 265: 13198). See also, U.S. Pat. No. 5,011,691; U.S. Pat. No. 5,266,683, Ozkaynak et al. (1990) *EMBO J.* 9: 2085–2093, Wharton et al. (1991) *PNAS* 88: 9214–9218), (Ozkaynak (1992) *J. Biol. Chem.* 267: 25220–25227 and U.S. Pat. No. 5,266,683); (Celeste etal. (1991) *PNAS* 87: 9843–9847); (Lyons et al. (1989) *PNAS* 86: 4554–4558). These disclosures describe the amino acid and DNA sequences, as well as the chemical and physical characteristics of these morphogenic proteins. See also Wozney et al. (1988) *Science* 242: 1528–1534); BMP-9 (WO 93/00432, published Jan. 7, 1993); DPP (Padgett et al. (1987) *Nature* 325: 81–84; and Vg-1 (Weeks (1987) *Cell* 51: 861–867).

Morphogens are expressed naturally in a variety of tissues during development, including those of the developing nervous system (Ozkaynak, et al. (1990) *EMBO J.* 9: 2085–2093; Ozkaynak, et al. (1991) *Biochem. Biophys. Res. Commun.* 179:116–123; Ozkaynak, et al. (1992) supra).

Vascular diseases of the nervous system rank first in frequency amongst all the neurologic diseases; they constitute about fifty percent of all neurologic hospital admissions to adult wards. The cardinal feature of cerebrovascular disease is the stroke, a term that connotes the sudden and dramatic development of a focal neurologic deficit. Obstruction of a nutrient artery supplying a locus of the central nervous system by, for example, a thrombus or an embolus or a failure of the systemic circulation and hypotension, if severe and prolonged enough, can deprive brain tissue of blood and oxygen, leading to disruption of physiologic function, subsequent death of neurons, and necrosis (infarction) of the affected locus. In hemorrhagic infarction, an extravasation of blood occurs into the brain tissue, the subarachnoid space, or both. Damage results from physical disruption of the region directly involved and pressure of the mass of blood on the surrounding tissue.

The neurologic deficit in a stroke reflects both the location and the size of the infarct or hemorrhage in the brain. Hemiplegia is the classic sign of vascular disease and occurs with strokes involving the cerebral hemisphere or the brainstem. However, depending on its location, a stroke may also give rise to many other manifestations accompanying or independent of hemiplegia, including numbness, sensory deficit, dysphasia, blindness, diplopia, dizziness, and dysarthria.

Patients who suffer a "stroke," or any other form of cerebral ischemic or traumatic injury, usually recover partially, but often remain mildly to severely debilitated. For example, total infarction of the middle cerebral artery in a human results in a contralateral hemiplegia, hemianesthesia, homonymous hemianopia, global or total sensorimotor aphasia (left hemisphere), and apractagnosia (right hemisphere). Once established, the motor, sensory, and language deficits usually remain static or very little improved after the passage of months or even years. Seldom can the patient ever again communicate effectively. Currently, aside from physical therapy, there is no treatment that reliably improves the prognosis of a patient who has suffered a stroke or any similar injury of the central nervous system.

SUMMARY OF THE INVENTION

The present invention is directed to methods and compositions for treatment of mammals afflicted with an ischemic or traumatic injury of the central nervous system. In particular, the invention provides treatments for mammals in whom central nervous system tissue has been damaged or lost due to stroke or a similar disruption in blood flow, or due to infliction of physical (e.g., mechanical) trauma affecting the central nervous system. The methods and compositions provided herein capitalize upon the discovery that administration of a morphogen to such a mammal provides significant improvement in central nervous system function, even when administered after central nervous system tissue has been damaged. The methods involve the administration of dimeric proteins defined as morphogens, inducers of these morphogens, or agonists of the corresponding morphogen receptors, or implantation of cells stimulated by exposure to the morphogens.

Accordingly, the invention features a method for treating a mammal who has suffered an injury to the central nervous system, such as a stroke or a traumatic injury. The method involves administering an effective dose of morphogen to the mammal at least six hours after the onset of the injury; for example, twelve, twenty-four, or forty-eight hours or even longer following the onset of injury.

The treatment regimen according to the invention is carried out in terms of administration mode, timing of the administration, and dosage, so that the functional recovery from impairment of the central nervous system is enhanced. The compositions of the present invention will contain therapeutically-effective amounts of the morphogen, morphogen inducers or agonists of morphogen receptors. That is, the compositions will contain an amount which provides appropriate concentrations of the agent to the affected nervous system tissue for a time sufficient to stimulate a detectable restoration of central nervous system function, up to and including a complete restoration thereof. The effective amount of morphogen can be provided in a single administration, in two administrations or in a plurality of administrations. Where the effective amount of morphogen is provided in a plurality of administrations, the morphogen is preferably administered to the mammal daily. In an alternative preferred embodiment, the morphogen is administered to the mammal biweekly (e.g., every three or four days). In a further alternative preferred embodiment, the morphogen is administered to the mammal once a week.

Practice of the invention confers significant clinical benefit on the afflicted mammal, in that the invention beneficially confers clinically relevant improvement in at least one of the mammal's motor coordination functions (e.g., posture, balance, grasp, gait), sensory perceptions (e.g., vision, touch, taste, olfaction, proprioception), or speech. Clinically relevant improvement can range from a detectable improvement to a complete restoration of an impaired or lost central nervous function.

The invention can be used to treat adverse consequences of central nervous system injuries that result from a variety of conditions. Thrombus, embolus, and systemic hypotension are among the most common causes of stroke. Other injuries may be caused by hypertension, hypertensive cerebral vascular disease, rupture of an aneurysm, an angioma, blood dyscrasia, cardiac failure, cardiac arrest, cardiogenic shock, kidney failure, septic shock, head trauma, spinal cord trauma, seizure, bleeding from a tumor, or other loss of blood volume and/or pressure. Administration of a morphogen according to the invention confers significant clinical benefit, even when administration occurs a significant amount of time following the injury.

Generally, the morphogens useful in the methods and compositions of the invention are dimeric proteins that induce morphogenesis of one or more eukaryotic (e.g., mammalian) cells, tissues or organs. Of particular interest herein are morphogens that induce morphogenesis at least of bone or neural tissue. Morphogens comprise a pair of polypeptides that, when folded, adopt a configuration sufficient for the resulting dimeric protein to elicit morphogenetic responses in cells and tissues displaying receptors specific for said morphogen. That is, the morphogens generally induce a cascade of events including all of the following in a morphogenically permissive environment: stimulating proliferation of progenitor cells; stimulating the differentiation of progenitor cells; stimulating the proliferation of differentiated cells; and supporting the growth and maintenance of differentiated cells. "Progenitor" cells are uncommitted cells that are competent to differentiate into one or more specific types of differentiated cells, depending on their genomic repertoire and the tissue specificity of the permissive environment in which morphogenesis is induced. Morphogens further can delay or mitigate the onset of senescence- or quiescence-associated loss of phenotype and/or tissue function. Morphogens still further can stimulate phenotypic expression of differentiated cells, including expression of metabolic and/or functional, e.g., secretory, properties thereof. In addition, morphogens can induce redifferentiation of committed cells under appropriate environmental conditions. As noted above, morphogens that induce proliferation and/or differentiation at least of neural tissue, and/or support the growth, maintenance and/or functional properties of neural tissue, are of particular interest herein. See, for example, WO 92/15323, WO 93/04692 and WO 94/03200 for more detailed disclosures as to the tissue morphogenic properties of these proteins.

As used herein, the terms "morphogen," "bone morphogen," "bone morphogenic protein," "BMP," "morphogenic protein" and "morphogenetic protein" all embrace the class of proteins typified by human osteogenic protein 1 (hOP-1). Nucleotide and amino acid sequences for hOP-1 are provided in SEQ ID NOs: 4 and 5, respectively. For ease of description, hOP-1 is recited herein below as a representative osteogenic protein. It will be appreciated by the artisan of ordinary skill in the art, however, that OP-1 merely is representative of the TGF-β subclass of true tissue morphogens competent to act as morphogenic proteins, and is not intended to limit the description. Other known, and useful proteins include, BMP-2, BMP-3, BMP-3b, BMP-4, BMP-5, BMP-6, BMP-8, BMP-9, BMP-10, BMP-11, BMP-12, BMP-13, BMP-15, GDF-1, GDF-2, GDF-3, GDF-5, GDF-6, GDF-7, GDF-8, GDF-9, GDF-10, GDF-11, GDF-12, NODAL, UNIVIN, SCREW, ADMP, NEURAL and morphogenically active amino acid variants thereof. Thus, in one embodiment, preferred morphogenic proteins, include but are not limited to, OP-1, OP-2, BMP-2, BMP-4, BMP-5, and BMP-6. In addition, as will be appreciated by the artisan of ordinary skill in the art any one of the morphogenic proteins recited herein also could be used as a reference sequence.

In another preferred embodiment, the proteins useful in the invention include biologically active species (phylogenetic) variants of any of the morphogenic proteins recited herein, including conservative amino acid sequence variants, proteins encoded by degenerate nucleotide sequence variants, and morphogenically active proteins sharing the conserved seven cysteine skeleton as defined herein and encoded by a DNA sequence competent to hybridize under standard stringency conditions to a DNA sequence encoding a morphogenic protein disclosed herein, including, without limitation, OP-1 and BMP-2 or BMP4. In still another embodiment, useful morphogens include those sharing the conserved seven cysteine domain and sharing at least 70% amino acid sequence homology (similarity) within the C-terminal active domain of a reference morphogen sequence, as defined herein below. In a preferred embodiment, the reference sequence is OP-1.

In still another embodiment, the morphogens useful in the methods and compositions of the invention can be defined as morphogenically active proteins having any one of the generic sequences defined herein, including OPX and Generic Sequences 7 and 8 (SEQ ID NOs: 1 and 2 respectively), or Generic Sequences 9 and 10 (SEQ ID NOs: 6 and 7, respectively). OPX accommodates the homologies between the various species of the osteogenic OP-1 and OP-2 proteins, and is described by the amino acid sequence presented herein below and in SEQ ID NO: 3. Generic sequence 9 is a 96 amino acid sequence containing the six cysteine skeleton defined by hOP-1 (residues 335–431 of SEQ ID NO: 5) and wherein the remaining residues accommodate the homologies of OP-1, OP-2, OP-3, BMP-2, BMP-3, BMP-4, BMP-5, BMP-6, BMP-8, BMP-9, BMP-10, BMP-11, BMP-15, GDF-1, GDF-3, GDF-5, GDF-6, GDF-7, GDF-8, GDF-9, GDF-10, GDF-11, UNIVIN, NODAL, DORSALIN, NEURAL, SCREW and ADMP. That is, each of the non-cysteine residues is independently selected from the corresponding residue in this recited group of proteins. Generic Sequence 10 is a 102 amino acid sequence which includes a 5 amino acid sequence added to the N-terminus of the Generic Sequence 9 and defines the seven cysteine skeleton defined by hOP-1 (330–431 SEQ ID NO: 5). Generic Sequences 7 and 8 are 96 and 102 amino acid sequences, respectively, containing either the six cysteine skeleton (Generic Sequence 7) or the seven cysteine skeleton (Generic Sequence 8) defined by hOP-1 and wherein the remaining residues non-cysteine accommodate the homologies of: OP-1, OP-2, OP-3, BMP-2, BMP-3, BMP-4, 60A, DPP, Vg1, BMP-5, BMP-6, Vgr-1, and GDF-1.

As contemplated herein, the family of morphogenic proteins described herein includes longer forms of a given protein, as well as phylogenetic, e.g., species and allelic variants, and biosynthetic mutants, including C-terminal addition and deletion mutants and variants, such as those which may alter the conserved C-terminal cysteine skeleton, provided that the alteration still allows the protein to form a dimeric species having a conformation capable of inducing neural tissue formation in a mammal when provided to a morphogenically permissive site in a mammal. In addition, the morphogenic proteins useful in the invention may include forms having varying glycosylation patterns and varying N-termini, may be naturally occurring or biosynthetically derived, and may be produced by expression of recombinant DNA in prokaryotic or eucaryotic host cells. The proteins are active as a single species (e.g., as homodimers, including chimeras), or combined as a mixed species, including heterodimers.

Of particular interest herein are morphogens which, when provided to neural tissue of a mammal, induce or maintain the normal state of differentiation and growth of that tissue. In a currently preferred demonstrative embodiment, the present morphogens induce or reinduce a developmental cascade of cellular and molecular events that culminates in the formation of vertebrate central nervous system tissue. In other preferred demonstrative embodiments, the present morphogens similarly induce the formation of other vertebrate (e.g., avian or mammalian) body tissues, such as but not limited to bone, cartilage, bone marrow, ligament, tooth dentin, periodontium, liver, kidney, lung, heart or gastrointestinal lining. The present demonstrations can be carried out in the context of developing, embryonic tissue, or at an aseptic, unscarred wound site in post-embryonic tissue. Particularly preferred morphogens induce or trigger a pattern formation cascade in a developing mammalian or avian embryo that culminates in the formation of one or more functionally integrated elements of central or peripheral nervous system. Such morphogens can be used to treat a mammal afflicted with ischemic or traumatic injury of the central nervous system.

The present invention alternatively can be practiced with methods and compositions comprising a morphogen inducer in lieu of a morphogen. A "morphogen inducer" is a compound that stimulates the in vivo production (i.e., transcription, translation, and/or secretion) of a therapeutically-effective concentration of an endogenous morphogen in the body of a mammal. An "effective" concentration is sufficient to promote the regeneration or maintenance of neural tissue and/or to inhibit additional loss thereof. Such compounds are understood to include substances which, when administered to a mammal, act on cells that normally are competent to produce and/or secrete a morphogen encoded within the genome of the mammal, and which cause the endogenous level of the morphogen to be increased. Endogenous or administered morphogens can act as endocrine, paracrine or autocrine factors. That is, endogenous morphogens can be synthesized by the cells in which the morphogenetic responses are induced, by neighboring cells, or by cells of a distant tissue, in which case the secreted endogenous morphogen is transported to the site of morphogenesis, e.g., by the individual's bloodstream. In preferred embodiments, the inducer stimulates expression and/or secretion of an endogenous morphogen so as to increase amounts thereof available in neural tissue.

In still other embodiments, an agent which acts as an agonist of a morphogen receptor may be administered instead of the morphogen itself. An "agonist" of a receptor is a compound which binds to the receptor, and for which the result of such binding is similar to the result of binding the natural, endogenous ligand of the receptor. That is, the compound must, upon interaction with the receptor, produce the same or substantially similar transmembrane and/or intracellular effects as the endogenous ligand. Thus, an agonist of a morphogen receptor binds to the receptor and such binding has the same or a functionally similar result as morphogen binding (e.g., induction of morphogenesis). The activity or potency of an agonist can be less than that of the natural ligand, in which case the agonist is said to be a "partial agonist," or it can be equal to or greater than that of the natural ligand, in which case it is said to be a "full agonist." Thus, for example, a small peptide or other molecule which can mimic the activity of a morphogen in binding to and activating the morphogen's receptor may be employed as an equivalent of the morphogen. Preferably the agonist is a full agonist, but partial morphogen receptor agonists may also be advantageously employed. Methods of identifying such agonists are known in the art and include assays for compounds which induce morphogen-mediated responses (e.g., induction of differentiation of metanephric mesenchyme, induction of endochondral bone formation, and the like). Such an agonist may also be referred to as a morphogen "mimic," "mimetic," or "analog."

The morphogens, inducers and agonists of the invention may be administered by any route of administration which is compatible with the selected agent, including by intravenous, subcutaneous, intramuscular, ophthalmic, intraperitoneal, buccal, rectal, vaginal, intraorbital, oral, intracerebral, intracranial, intraspinal, intraventricular, intrathecal, intracisternal, intracapsular, intranasal or by aerosol administration and may be formulated with any pharmaceutically acceptable carrier appropriate to the route of administration. In addition, various growth factors, hormones, enzymes, therapeutic compositions, antibiotics, or other bioactive agents can be co-administered with the morphogen. Thus, various known growth factors such as NGF, EGF, PDGF, IGF, FGF, TGF-$\alpha$, and TGF-$\beta$, as well as enzymes, enzyme inhibitors and/or chemoattractant/chemotactic factors, can be combined with the morphogen and be delivered to the defect locus.

The method of the invention advantageously stimulates restoration of central nervous system function even when practiced hours, or even days, following an injury to the central nervous system. The invention thus significantly improves on the treatment options available when central nervous system injury occurs and is not diagnosed or treated prior to the death of involved tissue.

The preferred methods, material, and examples that will now be described are illustrative only and are not intended to be limiting. Other features and advantages of the invention will be apparent from the following detailed description, and from the claims.

BRIEF DESCRIPTION OF THE DRAWINGS

FIG. 1. presents the percent amino acid sequence identity and percent amino acid sequence homology ("similarity") that various members of the family of morphogenic proteins as defined herein share with OP-1 in the C-terminal seven cysteine domain;

DETAILED DESCRIPTION OF PREFERRED EMBODIMENTS

A. General

Figure 2A:
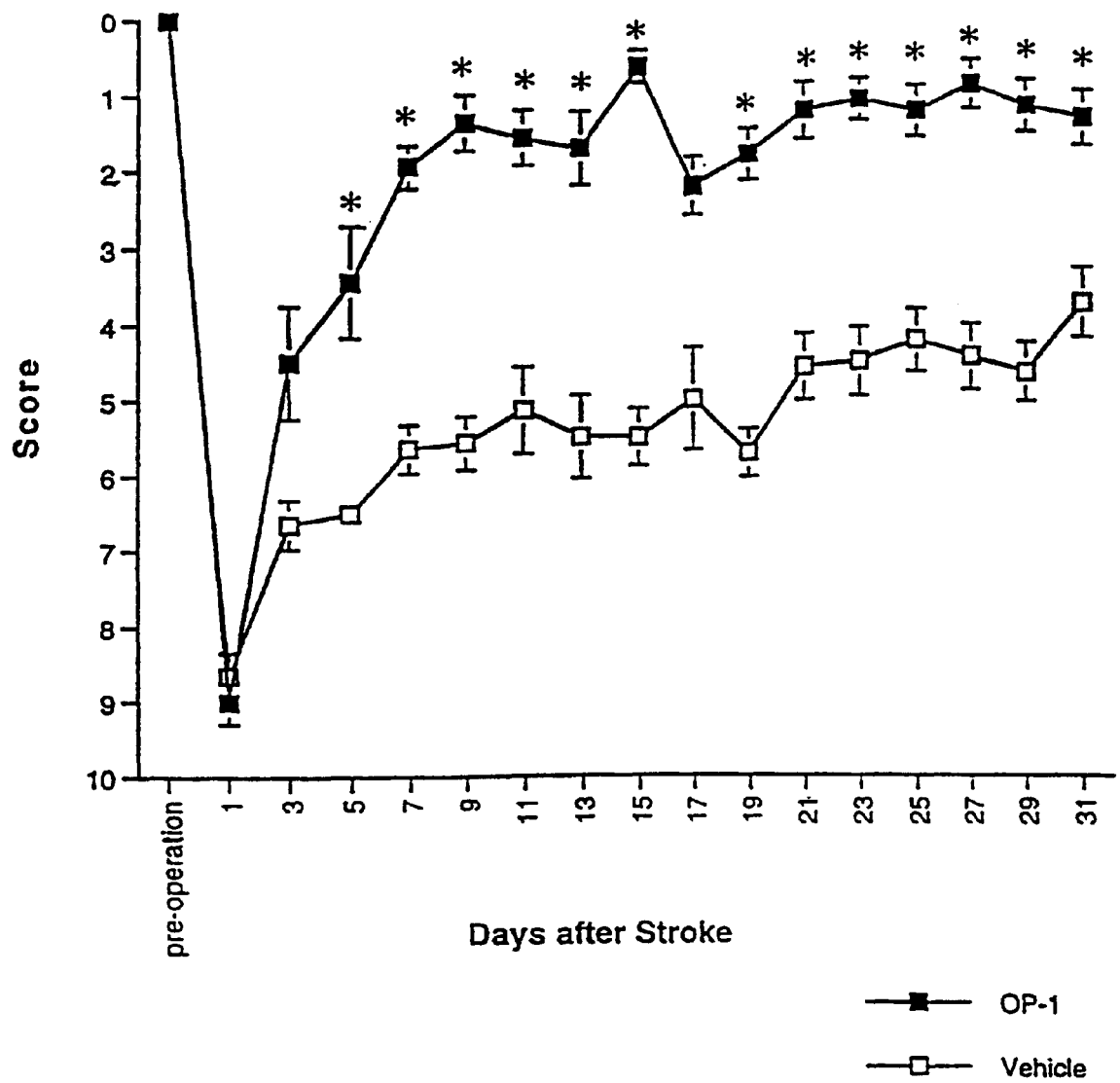
FIGS. 2A–2B are line graphs depicting forelimb placing (2A) and hindlimb placing (2B) scores of affected (left) limbs of OP-1 treated animals (10 $\mu$g/intracisternal injection; total OP-1 delivered in 8 injections=80 $\mu$g/animal; N=7; solid squares) and vehicle treated animals (N=7, open squares)
Figure 2B:
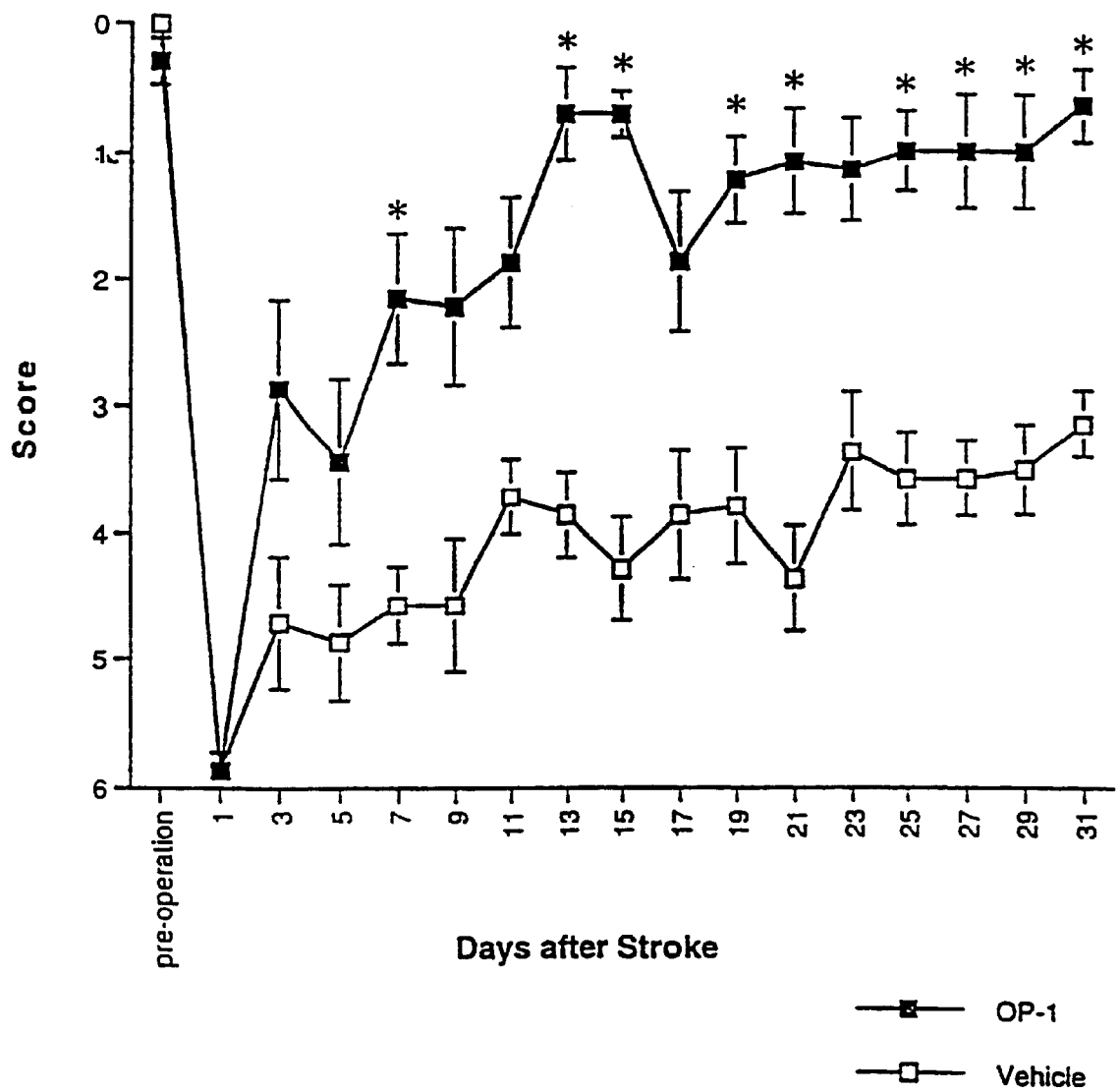
Figure 3A:
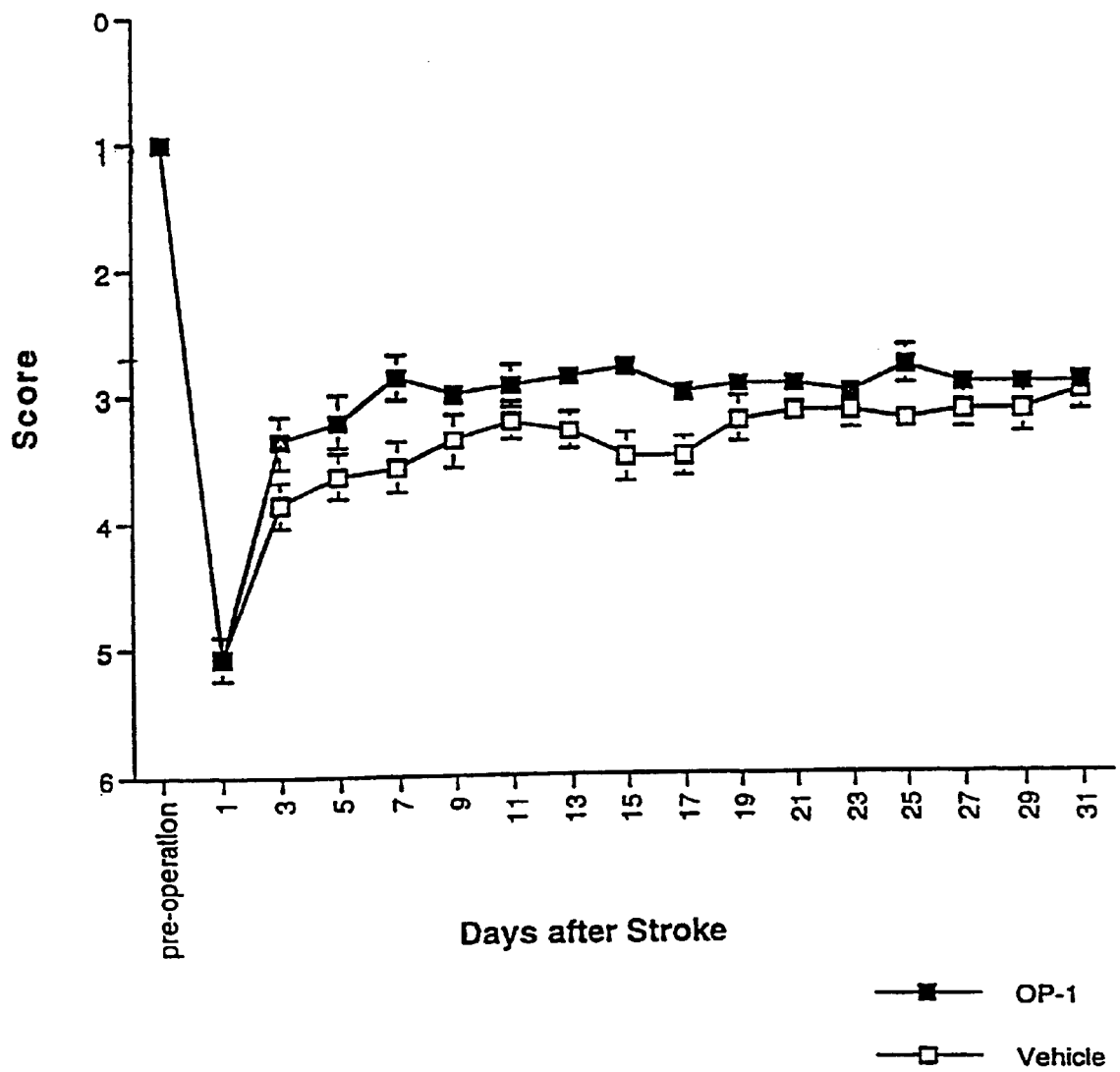
FIGS. 3A–3B are line graphs depicting balance beam (3A) and postural reflex (3B) scores in OP-1 treated animals (10 $\mu$g/intracisternal injection; total OP-1 delivered in 8 injections=80 $\mu$g/animal; N=7; solid squares) and vehicle treated animals (N=7 animals, open squares)
Figure 3B:
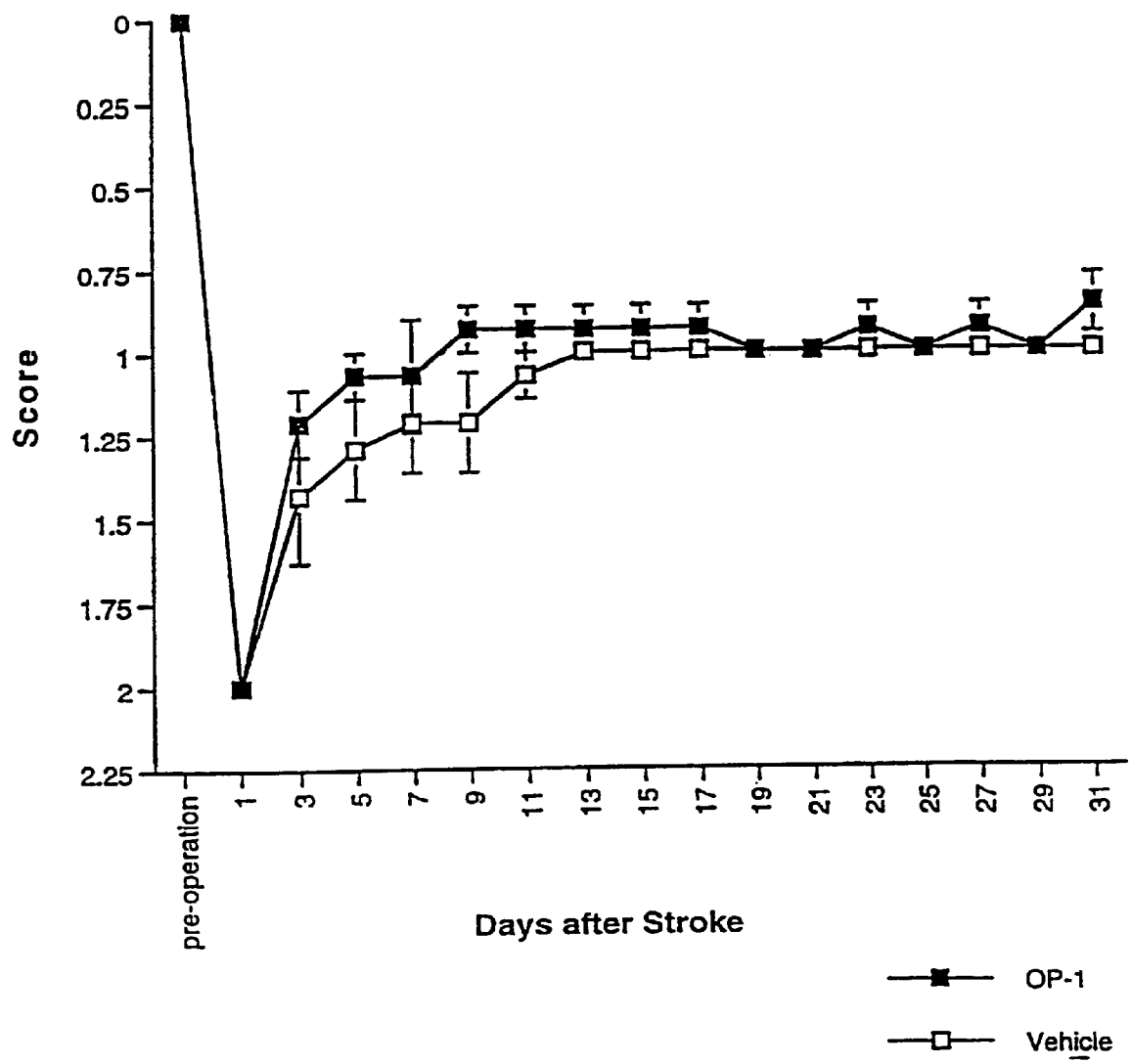

The present invention depends, in part, upon the surprising discovery that functional recovery following stroke or traumatic injury of the central nervous system is significantly enhanced by the administration of a morphogen, even when administered after affected tissue has succumbed to the injury and after central nervous system function has been impaired or lost. Most surprisingly, practice of the invention does not affect (e.g., reduce) the volume or extent of affected (infarcted) tissue. Thus, the invention capitalizes upon the discovery that functional central nervous system restoration can be achieved notwithstanding the loss of tissue originally occupying a stroke or traumatic injury loss. Significant (detectable; clinically relevant) restoration of CNS function can be obtained with even a single administration of a therapeutically-effective dose of a morphogen.

The invention features a method for treating a mammal who has suffered an injury to the central nervous system, such as stroke or a traumatic injury. The method involves administering a morphogen to the affected mammal at least six hours after onset of the injury; for example twelve, twenty-four, forty-eight hours, or even longer following injury. No practical end point the therapeutic window in which the invention can be practiced has yet been established. The invention can be used to treat one or more adverse consequences of central nervous system injury that arise from a variety of conditions. Thrombus, embolus, and systemic hypotension are among the most common causes of stroke. Other injuries may be caused by hypertension, hypertensive cerebral vascular disease, rupture of an aneurysm, an angioma, blood dyscrasia, cardiac failure, cardiac arrest, cardiogenic shock, kidney failure, septic shock, head trauma, spinal cord trauma, seizure, bleeding from a tumor, or other loss of blood volume or pressure. These injuries lead to disruption of physiologic function, subsequent death of neurons, and necrosis (infarction) of the affected areas. The term "stroke" connotes the resulting sudden and dramatic neurologic deficits associated with any of the foregoing injuries.

The terms "ischemia" or "ischemic episode," as used herein, mean any circumstance that results in a deficient supply of blood to a tissue. Thus, a central nervous system ischemic episode results from an insufficiency or interruption in the blood supply to any locus of the brain such as, but not limited to, a locus of the cerebrum, cerebellum or brain stem. The spinal cord, which is also a part of the central nervous system, is equally susceptible to ischemia resulting from diminished blood flow. An ischemic episode may be caused by a constriction or obstruction of a blood vessel, as occurs in the case of a thrombus or embolus. Alternatively, the ischemic episode may result from any form of compromised cardiac function, including cardiac arrest, as described above. Where the deficiency is sufficiently severe and prolonged, it can lead to disruption of physiologic function, subsequent death of neurons, and necrosis (infarction) of the affected areas. The extent and type of neurologic abnormality resulting from the injury depend on the location and size of the infarct or the focus of ischemia. Where the ischemia is associated with a stroke, it can be either global or focal in extent.

The term "focal ischemia," as used herein in reference to the central nervous system, means the condition that results from the blockage of a single artery that supplies blood to the brain or spinal cord, resulting in the death of all cellular elements (pan-necrosis) in the territory supplied by that artery.

The term "global ischemia," as used herein in reference to the central nervous system, means the condition that results from a general diminution of blood flow to the entire brain, forebrain, or spinal cord, which causes the delayed death of neurons, particularly those in metabolically active loci, throughout these tissues. The pathology in each of these cases is quite different, as are the clinical correlates. Models of focal ischemia apply to patients with focal cerebral infarction, while models of global ischemia are analogous to cardiac arrest, and other causes of systemic hypotension.

It is expected that the invention will also be useful for treating traumatic injuries to the central nervous system that are caused by mechanical forces, such as a blow to the head. Trauma can involve a tissue insult selected from abrasion, incision, contusion, puncture, compression, etc., such as can arise from traumatic contact of a foreign object with any locus of or appurtenant to the mammalian head, neck or vertebral column. Other forms of traumatic injury can arise from constriction or compression of mammalian CNS tissue by an inappropriate accumulation of fluid (e.g., a blockade or dysfunction of normal cerebrospinal fluid or vitreous humor fluid production, turnover or volume regulation, or a subdural or intracranial hematoma or edema). Similarly, traumatic constriction or compression can arise from the presence of a mass of abnormal tissue, such as a metastatic or primary tumor.

B. Biochemical, Structural and Functional Properties of Useful Morphogenic Proteins As noted above, a protein is morphogenic as defined herein if it induces the developmental cascade of cellular and molecular events that culminate in the formation of new, organ-specific tissue. In one preferred embodiment, a morphogen is a dimeric protein comprising a pair of polypeptide chains, each chain having a sequence that corresponds to or is functionally equivalent to at least the conserved C-terminal six or seven cysteine skeleton of human OP-1, included in SEQ ID NO: 5, and/or which shares 70% amino acid sequence homology with OP-I in this region. The morphogens generally are competent to induce a cascade of events including all of the following, in a morphogenically permissive environment: stimulating proliferation of progenitor cells; stimulating the differentiation of progenitor cells; stimulating the proliferation of differentiated cells; and supporting the growth and maintenance of differentiated cells. Under appropriate conditions the morphogens also are competent to induce redifferentiation of committed cells, particularly of cells that have strayed from their "normal" differentiation pathway. Details of how the morphogens useful in this invention first were identified, as well as a description on how to make, use and test them for morphogenic activity are disclosed in numerous publications, including U.S. Pat. Nos. 5,011,691, 5,266,683, and the international application publications WO 92/15323; WO 93/04692; WO 94/03200. As disclosed therein, the morphogens can be purified from naturally-sourced material or recombinantly produced from prokaryotic or eukaryotic host cells, using the genetic sequences disclosed therein. Alternatively, novel morphogenic sequences can be identified following the procedures disclosed therein.

Naturally occurring proteins identified and/or appreciated herein to be true tissue morphogenic proteins and useful in the methods and compositions of the invention form a distinct subgroup within the loose evolutionary grouping of sequence-related proteins known as the TGF-β superfamily or supergene family. The naturally occurring morphogens share substantial amino acid sequence homology in their C-terminal regions (domains). Typically, the above-mentioned naturally occurring morphogens are translated as a precursor, having an N-terminal signal peptide sequence, typically less than about 35 residues in length, followed by a "pro" domain that is cleaved to yield the mature protein, which includes the biologically active C-terminal domain. The signal peptide is cleaved rapidly upon translation, at a cleavage site that can be predicted in a given sequence using the method of Von Heijne (1986) *Nucleic Acids Research* 14: 4683–30 4691. The pro domain typically is about three times larger than the fully processed mature C-terminal domain. Under native conditions the protein is secreted as a mature dimer and the cleaved pro domain can be associated therewith to form a protein complex, presumably to improve the solubility of the mature dimeric protein. Typically, the complex form of a morphogen is more soluble than the mature form under physiological conditions.

Natural-sourced morphogenic protein in its mature, native form, typically is a glycosylated dimer, typically having an apparent molecular weight of about 30–36 kDa as determined by SDS-PAGE. When reduced, the 30 kDa protein gives rise to two glycosylated polypeptide subunits having apparent molecular weights in the range of about 16 kDa and 18 kDa. The unglycosylated dimeric protein, which also has morphogenic activity, typically has an apparent molecular weight in the range of about 27 kDa. When reduced, the 27 kDa protein gives rise to two unglycosylated polypeptides having molecular weights typically in the range of about 14 kDa to 16 kDa.

In preferred embodiments, the each of the polypeptide chains of a dimeric morphogenic protein as defined herein comprises an amino acid sequence sharing a defined relationship with an amino acid sequence of a reference morphogen. In one embodiment, preferred morphogenic polypeptide chains share a defined relationship with a sequence present in morphogenically active human OP-1, SEQ ID NO: 5. However, any one or more of the naturally occurring or biosynthetic morphogenic proteins disclosed herein similarly could be used as a reference sequence. Preferred morphogenic polypeptide chains share a defined relationship with at least the C-terminal six cysteine domain of human OP-1, residues 335–431 of SEQ ID NO: 5. Preferably, morphogenic polypeptide chains share a defined relationship with at least the C-terminal seven cysteine domain of human OP-1, residues 330–431 of SEQ ID NO: 5. That is, preferred polypeptide chains in a dimeric protein with tissue morphogenic activity each comprise a sequence that corresponds to a reference sequence or is functionally equivalent thereto.

Functionally equivalent sequences include functionally equivalent arrangements of cysteine residues disposed within the reference sequence, including amino acid insertions or deletions which alter the linear arrangement of these cysteines, but do not materially impair their relationship in the folded structure of the dimeric morphogen protein, including their ability to form such intra- or inter-chain disulfide bonds as may be necessary for morphogenic activity. For example naturally occurring morphogens have been described in which at least one internal deletion (of one residue; BMP2) or insertion (of four residues; GDF-1) is present but does not abrogate biological activity. Functionally equivalent sequences further include those wherein one or more amino acid residues differ from the corresponding residue of a reference sequence, e.g., the C-terminal seven cysteine domain (also referred to herein as the conserved seven cysteine skeleton) of human OP-1, provided that this difference does not destroy tissue morphogenic activity. Accordingly, conservative substitutions of corresponding amino acids in the reference sequence are preferred. Amino acid residues that are "conservative substitutions" for corresponding residues in a reference sequence are those that are physically or functionally similar to the corresponding reference residues, e.g., that have similar size, shape, electric charge, chemical properties including the ability to form covalent or hydrogen bonds, or the like. Particularly preferred conservative substitutions are those fulfilling the criteria defined for an accepted point mutation in Dayhoff et al. (1978), 5 *Atlas of Protein Sequence and Structure*, Suppl. 3, ch. 22 (pp. 354–352), Natl. Biomed. Res. Found., Washington, D.C. 20007, the teachings of which are incorporated by reference herein. Examples of conservative substitutions include: Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. The term "conservative variation" also includes the use of a substituted amino acid in place of an unsubstituted parent amino acid provided that antibodies raised to the substituted polypeptide also immunoreact with the unsubstituted polypeptide.

As described elsewhere herein, the class of morphogenic proteins useful in the methods and compositions of the invention is typified by human osteogenic protein (hOP-1). Other morphogenic proteins useful in the practice of the invention include morphogenically active forms of OP-1, OP-2, OP-3, BMP-2, BMP-3, BMP-4, BMP-5, BMP-6, BMP-9, DPP, Vg1, Vgr, 60A protein, GDF-1, GDF-3, GDF-5, GDF-6, GDF-7, BMP-10, BMP-11, BMP-13, BMP-15, UNIVIN, NODAL, SCREW, ADMP or NEURAL and amino acid sequence variants thereof. In one currently preferred embodiment, osteogenic protein include any one of: OP-1, OP-2, OP-3, BMP-2, BMP-4, BMP-5, BMP-6, BMP-9, and amino acid sequence variants and homologs thereof, including species homologs, thereof.

Publications disclosing these sequences, as well as their chemical and physical properties, include: OP-1 and OP-2: U.S. Pat. No. 5,011,691, U.S. Pat. No. 5,266,683, Ozkaynak et al. (1990) *EMBO J*. 9: 2085–2093; OP-3: WO 94/10203 (PCT US93/10520); BMP-2, BMP-3, BMP-4: WO 88/00205, Wozney et al. (1988) *Science* 242: 1528–1534); BMP-5 and BMP-6: Celeste et al. (1991) *PNAS* 87: 9843–9847; Vgr-1: Lyons et al. (1989) *PNAS* 86: 4554–4558; DPP: Padgett et al. (1987) *Nature* 325: 81–84; Vg-1: Weeks (1987) *Cell* 51: 861–867; BMP-9: WO 95/33830 (PCT/US95/07084); BMP-10: WO 94/26893 (PCT/US94/05290); BMP-11: WO 94/26892 (PCT/US94/05288); BMP-12: WO 95/16035 (PCT/US94/14030); BMP-13: WO 95/16035 (PCT/US94/14030); GDF-1: WO 92/00382 (PCT/US91/04096) and Lee et al. (1991) *PNAS* 88: 4250–4254; GDF-8: WO 94/21681 (PCT/US94/03019); GDF-9: WO 94/15966 (PCT/US94/00685); GDF-10: WO 95/10539 (PCT/US94/11440); GDF-11: WO 96/01845 (PCT/US95/08543); BMP-15: WO 96/36710 (PCT/US96/06540); MP121: WO 96/01316 (PCT/EP95/02552); GDF-5 (CDMP-1, MP52): WO 94/15949 (PCT/US94/00657) and WO 96/14335 (PCT/US94/12814) and WO 93/16099 (PCT/EP93/00350); GDF-6 (CDMP-2, BMP-13): WO 95/01801 (PCT/US94/07762) and WO 96/14335 and WO 95/10635 (PCT/US94/14030); GDF-7 (CDMP-3, BMP-12): WO 95/10802 (PCT/US94/07799) and WO 95/10635 (PCT/US94/14030). In another embodiment, useful proteins include biologically active biosynthetic constructs, including novel biosynthetic morphogenic proteins and chimeric proteins designed using sequences from two or more known morphogens. See also the biosynthetic constructs disclosed in U.S. Pat. No. 5,011,691, the disclosure of which is incorporated herein by reference (e.g., COP-1, COP-3, COP-4, COP-5, COP-7, and COP-16).

In certain preferred embodiments, useful morphogenic proteins include those in which the amino acid sequences comprise a sequence sharing at least 70% amino acid sequence homology or "similarity", and preferably 80% homology or similarity with a reference morphogenic protein selected from the foregoing naturally occurring proteins. Preferably, the reference protein is human OP-1, and the reference sequence thereof is the C-terminal seven cysteine domain present in osteogenically active forms of human OP-1, residues 330–431 of SEQ ID NO: 5. Useful morphogenic proteins accordingly include allelic, phylogenetic counterpart and other variants of the preferred reference sequence, whether naturally-occurring or biosynthetically produced (e.g., including "muteins" or "mutant proteins"), as well as novel members of the general morphogenic family of proteins including those set forth and identified above. Certain particularly preferred morphogenic polypeptides share at least 60% amino acid identity with the preferred reference sequence of human OP-1, still more preferably at least 65% amino acid identity therewith.

In certain embodiments, a polypeptide suspected of being functionally equivalent to a reference morphogen polypeptide is aligned therewith using the method of Needleman, et al. (1970) *J. Mol. Biol.* 48:443–453, implemented conveniently by computer programs such as the Align program (DNAstar, Inc.). As noted above, internal gaps and amino acid insertions in the candidate sequence are ignored for purposes of calculating the defined relationship, conventionally expressed as a level of amino acid sequence homology or identity, between the candidate and reference sequences. "Amino acid sequence homology" is understood herein to include both amino acid sequence identity and similarity. Homologous sequences share identical and/or similar amino acid residues, where similar residues are conservation substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence. In a currently preferred embodiment, the reference sequence is OP-1.

FIG. 1 recites the percent amino acid sequence homology (similarity) and percent identity within the C-terminal seven cysteine domain of various representative members of the TGF-β family, using OP-1 as the reference sequence. The percent homologies recited in the figure are calculated with the sequences aligned essentially following the method of Needleman, et al. (1970) *J. Mol. Biol.*, 48: 443–453, calculated using the Align Program (DNAstar, Inc.). Insertions and deletions from the reference morphogen sequence, here the C-terminal, biologically active seven-cysteine domain or skeleton of hOP-1, are ignored for purposes of calculation.

As is apparent to one of ordinary skill in the art reviewing the sequences for the proteins listed in FIG. 1, significant amino acid changes can be made from the reference sequence while retaining morphogenic activity. For example, while the GDF-1 protein sequence shares only about 50% amino acid identity with the hOP-1 sequence described herein, the GDF-1 sequence shares greater than 70% amino acid sequence homology with the hOP-1 sequence, where "homology" is as defined above. Moreover, GDF-1 contains a four amino acid insert (Gly-Gly-Pro-Pro) between the two residues corresponding to residue 372 and 373 of OP-1 (SEQ ID NO: 5). Similarly, BMP-3 has a "extra" residue, a valine, inserted between the two residues corresponding to residues 385 and 386 of hOP-1 (SEQ ID NO: 5). Also, BMP-2 and BMP-4 both are "missing" the amino acid residue corresponding to residue 389 of OP-1 (SEQ ID NO: 5). None of these "deviations" from the reference sequence appear to interfere with biological activity.

In other preferred embodiments, the family of morphogenic polypeptides useful in the present invention, and members thereof, are defined by a generic amino acid sequence. For example, Generic Sequence 7 (SEQ ID NO: 1) and Generic Sequence 8 (SEQ ID NO: 2) disclosed below, accommodate the homologies shared among preferred protein family members identified to date, including at least OP-1, OP-2, OP-3, CBMP-2A, CBMP-2B, BMP-3, 60A, DPP, Vgl, BMP-5, BMP-6, Vgr-1, and GDF-1. The amino acid sequences for these proteins are described herein and/or in the art, as summarized above. The generic sequences include both the amino acid identity shared by these sequences in the C-terminal domain, defined by the six and seven cysteine skeletons (Generic Sequences 7 and 8, respectively), as well as alternative residues for the variable positions within the sequence. The generic sequences provide an appropriate cysteine skeleton where inter- or intramolecular disulfide bonds can form, and contain certain critical amino acids likely to influence the tertiary structure of the folded proteins. In addition, the generic sequences allow for an additional cysteine at position 36 (Generic Sequence 7) or position 41 (Generic Sequence 8), thereby encompassing the morphogenically active sequences of OP-2 and OP-3.

```
Generic Sequence 7 (SEQ ID NO: 1)
        Leu Xaa Xaa Xaa Phe Xaa Xaa
         1                5
Xaa Gly Trp Xaa Xaa Xaa Xaa Xaa Xaa Pro
        10                      15
Xaa Xaa Xaa Xaa Ala Xaa Tyr Cys Xaa Gly
        20                      25
Xaa Cys Xaa Xaa Pro Xaa Xaa Xaa Xaa Xaa
        30                      35
Xaa Xaa Xaa Asn His Ala Xaa Xaa Xaa Xaa
        40                      45
Xaa Xaa Xaa Xaa Xaa Xaa Xaa Xaa Xaa Xaa
        50                      55
Xaa Xaa Xaa Cys Cys Xaa Pro Xaa Xaa Xaa
        60                      65
Xaa Xaa Xaa Xaa Xaa Leu Xaa Xaa Xaa Xaa
        70                      75
Xaa Xaa Xaa Val Xaa Leu Xaa Xaa Xaa Xaa
        80                      85
Xaa Met Xaa Val Xaa Xaa Cys Xaa Cys Xaa
        90                      95
``` wherein each Xaa independently is selected from a group of one or more specified amino acids defined as follows: "Res." means "residue" and Xaa at res. 2=(Tyr or Lys); Xaa at res. 3=Val or Ile); Xaa at res. 4=(Ser, Asp or Glu); Xaa at res. 6 =(Arg, Gln, Ser, Lys or Ala); Xaa at res. 7=(Asp or Glu); Xaa at res. 8=(Leu, Val or Ile); Xaa at res. 11=(Gln, Leu, Asp, His, Asn or Ser); Xaa at res. 12 =(Asp, Arg, Asn or Glu); Xaa at res. 13=(Trp or Ser); Xaa at res. 14=(Ile or Val); Xaa at res. 15=(Ile or Val); Xaa at res. 16=(Ala or Ser); Xaa at res. 18=(Glu, Gln, Leu, Lys, Pro or Arg); Xaa at res. 19=(Gly or Ser); Xaa t res. 20=(Tyr or Phe); Xaa at res. 21=(Ala, Ser, Asp, Met, His, Gln, Leu or Gly); Xaa at res. 23=(Tyr, Asn or Phe); Xaa at res. 26=(Glu, His, Tyr, Asp, Gln, Ala or Ser); Xaa at res. 28=(Glu, Lys, Asp, Gln or Ala); Xaa at res. 30=(Ala, Ser, Pro, Gln, Ile or Asn); Xaa at res. 31=(Phe, Leu or Tyr); Xaa at res. 33=(Leu, Val or Met); Xaa at res. 34=(Asn, Asp, Ala, Thr or Pro); Xaa at res. 35=(Ser, Asp, Glu, Leu, Ala or Lys); Xaa at res. 36=(Tyr, Cys, His, Ser or Ile); Xaa at res. 37=(Met, Phe, Gly or Leu); Xaa at res. 38=(Asn, Ser or Lys); Xaa at res. 39=(Ala, Ser, Gly or Pro); Xaa at res. 40=(Thr, Leu or Ser); Xaa at res. 44=(Ile, Val or Thr); Xaa at res. 45=(Val, Leu, Met or Ile); Xaa at res. 46=(Gln or Arg); Xaa at res. 47=(Thr, Ala or Ser); Xaa at res. 48=(Leu or Ile); Xaa at res. 49=(Val or Met); Xaa at res. 50=(His, Asn or Arg); Xaa at res. 51=(Phe, Leu, Asn, Ser, Ala or Val); Xaa at res. 52=(Ile, Met, Asn, Ala, Val, Gly or Leu); Xaa at res. 53=(Asn, Lys, Ala, Glu, Gly or Phe); Xaa at res. 54=(Pro, Ser or Val); Xaa at res. 55=(Glu, Asp, Asn, Gly, Val, Pro or Lys); Xaa at res. 56=(Thr, Ala, Val, Lys, Asp, Tyr, Ser, Gly, Ile or His); Xaa at res. 57=(Val, Ala or Ile); Xaa at res. 58=(Pro or Asp); Xaa at res. 59=(Lys, Leu or Glu); Xaa at res. 60=(Pro, Val or Ala); Xaa at res. 63=(Ala or Val); Xaa at res. 65=(Thr, Ala or Glu); Xaa at res. 66=(Gln, Lys, Arg or Glu); Xaa at res. 67=(Leu, Met or Val); Xaa at res. 68=(Asn, Ser, Asp or Gly); Xaa at res. 69=(Ala, Pro or Ser); Xaa at res. 70=(Ile, Thr, Val or Leu); Xaa at res. 71=(Ser, Ala or Pro); Xaa at res. 72=(Val, Leu, Met or Ile); Xaa at res. 74=(Tyr or Phe); Xaa at res. 75=(Phe, Tyr, Leu or His); Xaa at res. 76=(Asp, Asn or Leu); Xaa at res. 77=(Asp, Glu, Asn, Arg or Ser); Xaa at res. 78=(Ser, Gln, Asn, Tyr or Asp); Xaa at res. 79=(Ser, Asn, Asp, Glu or Lys); Xaa at res. 80=(Asn, Thr or Lys); Xaa at res. 82=(Ile, Val or Asn); Xaa at res. 84=(Lys or Arg); Xaa at res. 85=(Lys, Asn, Gln, His, Arg or Val); Xaa at res. 86=(Tyr, Glu or His); Xaa at res. 87=(Arg, Gln, Glu or Pro); Xaa at res. 88=(Asn, Glu, Trp or Asp); Xaa at res. 90=(Val, Thr, Ala or Ile); Xaa at res. 92=(Arg, Lys, Val, Asp, Gln or Glu); Xaa at res. 93=(Ala, Gly, Glu or Ser); Xaa at res. 95=(Gly or Ala) and Xaa at res. 97=(His or Arg).

Generic Sequence 8 (SEQ ID NO: 2) includes all of Generic Sequence 7 (SEQ ID NO: 1) and in addition includes the following sequence (SEQ ID NO: 8) at its N-terminus:

```
          SEQ ID NO: 8
        Cys Xaa Xaa Xaa Xaa
         1               5
```

Accordingly, beginning with residue 7, each "Xaa" in Generic Sequence 8 is a specified amino acid defined as for Generic Sequence 7, with the distinction that each residue number described for Generic Sequence 7 is shifted by five in Generic Sequence 8. Thus, "Xaa at res. 2=(Tyr or Lys)" in Generic Sequence 7 refers to Xaa at res. 7 in Generic Sequence 8. In Generic Sequence 8, Xaa at res. 2=(Lys, Arg, Ala or Gln); Xaa at res. 3=(Lys, Arg or Met); Xaa at res. 4=(His, Arg or Gln); and Xaa at res. 5=(Glu, Ser, His, Gly, Arg, Pro, Thr, or Tyr).

In another embodiment, useful osteogenic proteins include those defined by Generic Sequences 9 and 10 (SEQ ID NOs: 6 and 7, respectively), described herein above. Specifically, Generic Sequences 9 and 10 are composite amino acid sequences of the following proteins: human OP-1, human OP-2, human OP-3, human BMP-2, human BMP-3, human BMP-4, human BMP-5, human BMP-6, human BMP-8, human BMP-9, human BMP-10, human BMP-11, Drosophila 60A, Xenopus Vg-1, sea urchin UNIVIN, human CDMP-1 (mouse GDF-5), human CDMP-2 (mouse GDF-6, human BMP-13), human CDMP-3 (mouse GDF-7, human BMP-12), mouse GDF-3, human GDF-1, mouse GDF-11, chicken DORSALIN, Drosophila dpp, Drosophila SCREW, mouse NODAL, mouse GDF-8, human GDF-8, mouse GDF-9, mouse GDF-10, human GDF- 11, mouse GDF-11, human BMP-15, and rat BMP-3b. Like Generic Sequence 7, Generic Sequence 9 accommodates the C-terminal six cysteine skeleton and, like Generic Sequence 8, Generic Sequence 10 accommodates the seven cysteine skeleton.

```
        Generic Sequence 9 (SEQ ID NO: 6)
Xaa Xaa Xaa Xaa Xaa Xaa Xaa Xaa Xaa Xaa
 1               5                      10
Xaa Xaa Xaa Xaa Xaa Xaa Pro Xaa Xaa Xaa
                15                      20
Xaa Xaa Xaa Xaa Cys Xaa Gly Xaa Cys Xaa
                25                      30
Xaa Xaa Xaa Xaa Xaa Xaa Xaa Xaa Xaa Xaa
                35                      40
Xaa Xaa Xaa Xaa Xaa Xaa Xaa Xaa Xaa Xaa
                45                      50
Xaa Xaa Xaa Xaa Xaa Xaa Xaa Xaa Xaa Xaa
                55                      60
Xaa Cys Xaa Pro Xaa Xaa Xaa Xaa Xaa Xaa
                65                      70
Xaa Xaa Leu Xaa Xaa Xaa Xaa Xaa Xaa Xaa
                75                      80
Xaa Xaa Xaa Xaa Xaa Xaa Xaa Xaa Xaa Xaa
                85                      90
Xaa Xaa Xaa Cys Xaa Cys Xaa
                95
``` wherein each Xaa is independently selected from a group of one or more specified amino acids defined as follows: "Res." means "residue" and Xaa at res. 1=(Phe, Leu or Glu); Xaa at res. 2=(Try, Phe, His, Arg, Thr, Lys, Gln, Val or Glu); Xaa at res. 3=(Val, Ile, Leu or Asp); Xaa at res. 4=(Ser, Asp, Glu, Asn, or Phe); Xaa at res. 5 (Phe or Glu); Xaa at res. 6=(Arg, Gln, Lys, Ser, Ala or Asn); Xaa at res. 7=(Asp, Glu, Leu, Ala or Gln); Xaa at res. 8=(Leu, Val, Met, Ile or Phe); Xaa at res. 9=(Gly, His or Lys); Xaa at res. 10=(Trp or Met); Xaa at res. 11=(Gln, Leu, His, Glu, Asn, Asp, Ser or Gly); Xaa at res. 12=(Asp, Asn, Ser, Lys, Arg, Glu or His); Xaa at res. 13=(Trp or Ser); Xaa at res. 14=(Ile, or Val); Xaa at res. 15=(Ile or Val); Xaa at res. 16=(Ala, Ser, Tyr or Trp); Xaa at res. 18=(Glu, Lys, Gln, Met, Pro, Leu, Arg, His or Lys); Xaa at res. 19=(Gly, Glu, Asp, Lys, Ser, Gln, Arg or Phe); Xaa at res. 20=(Tyr or Phe); Xaa at res. 21=(Ala, Ser, Gly, Met, Gln, His, Glu, Asp, Ley, Asn, Lys or Thr); Xaa at res. 22=(Ala or Pro); Xaa at res. 23=(Tyr, Phe, Asn, Ala or Arg); Xaa at res. 24=(Tyr, His, Glu, Phe or Arg); Xaa at res. 26=(Glu, Asp, Ala, Ser, Tyr, His, Lys, Arg, Gln or Gly); Xaa at res. 28 =(Glu, Asp, Ley, Val, Lys, Gly, Thr, Ala or Gln); Xaa at res. 30=(Ala, Ser, Ile, Asn, Pro, Glu, Asp, Phe, Gln, or Leu); Xaa at res. 31=(Phe, Tyr, Leu, Asn, Gly or Arg); Xaa at res. 32=(Pro,Ser, Ala or Val); Xaa at res. 33=(Leu, Met, Glu, Phe or Val); Xaa at res. 34=(Asn, Asp, Thr, Gly, Ala, Arg, Leu or Pro); Xaa at res. 35=(Ser, Ala, Glu, Asp, Thr, Leu, Lys, Gln or His); Xaa at res. 36=(Tyr, His, Cys, Ile, Arg, Asp, Asn, Lys, Ser, Glu or Gly); Xaa at res. 37=(Met, Leu, Phe, Val, Gly or Tyr); Xaa at res. 38=(Asn, Glu, Thr, Pro, Lys, His, Gly, Met, Val or Arg); Xaa at res. 39=(Ala, Ser, Gly, Pro or Phe); Xaa at res. 40=(Thr, Ser, Leu, Pro, His or Met); Xaa at res. 41=(Asn, Lys, Val, Thr or Gln); Xaa at res. 42=(His, Tyr or Lys); Xaa at res. 43=(Ala, Thr, Leu or Tyr); Xaa at res. 44=(Ile, Thr, Val, Phe, Tyr, Met or Pro); Xaa at res. 45=(Val, Leu, Met, Ile or His); Xaa at res. 46=(Gln, Arg or Thr); Xaa at res. 47=(Thr, Ser, Ala, Asn or His); Xaa at res. 48=(Leu, Asn or Ile); Xaa at res. 49=(Val, Met, Leu, Pro or Ile); Xaa at res. 50=(His, Asn, Arg, Lys, Tyr or Gln); Xaa at res. 51=(Phe, Leu, Ser, Asn, Met, Ala, Arg, Glu, Gly or Gln); Xaa at res. 52=(Ile, Met, Leu, Val, Lys, Gln, Ala or Tyr); Xaa at res. 53=(Asn, Phe, Lys, Glu, Asp, Ala, Gln, Gly, Leu or Val); Xaa at res. 54=(Pro, Asn, Ser, Val or Asp); Xaa at res. 55=(Glu, Asp, Asn, Lys, Arg, Ser, Gly, Thr, Gln, Pro or His); Xaa at res. 56=(Thr, His, Tyr, Ala, Ile, Lys, Asp, Ser, Gly or Arg); Xaa at res. 57=(Val, Ile, Thr, Ala, Leu or Ser); Xaa at res. 58=(Pro, Gly, Ser, Asp or Ala); Xaa at res. 59=(Lys, Leu, Pro, Ala, Ser, Glu, Arg or Gly); Xaa at res. 60=(Pro, Ala, Val, Thr or Ser); Xaa at res. 61=(Cys, Val or Ser); Xaa at res. 63=(Ala, Val or Thr); Xaa at res. 65=(Thr, Ala, Glu, Val, Gly, Asp or Tyr); Xaa at res. 66=(Gln, Lys, Glu, Arg or Val); Xaa at res. 67=(Leu, Met, Thr or Tyr); Xaa at res. 68=(Asn, Ser, Gly, Thr, Asp, Glu, Lys or Val); Xaa at res. 69=(Ala, Pro, Gly or Ser); Xaa at res. 70=(Ile, Thr, Leu or Val); Xaa at res. 71=(Ser, Pro, Ala, Thr, Asn or Gly); Xaa at res. 2=(Val, Ile, Leu or Met); Xaa at res. 74=(Tyr, Phe, Arg, Thr, Tyr or Met); Xaa at res. 75=(Phe, Tyr, His, Leu, Ile, Lys, Gln or Val); Xaa at res. 76=(Asp, Leu, Asn or Glu); Xaa at res. 77=(Asp, Ser, Arg, Asn, Glu, Ala, Lys, Gly or Pro); Xaa at res. 78=(Ser, Asn, Asp, Tyr, Ala, Gly, Gln, Met, Glu, Asn or Lys); Xaa at res. 79=(Ser, Asn, Glu, Asp, Val, Lys, Gly, Gln or Arg); Xaa at res. 80=(Asn, Lys, Thr, Pro, Val, Ile, Arg, Ser or Gln); Xaa at res. 81=(Val, Ile, Thr or Ala); Xaa at res. 82=(Ile, Asn, Val, Leu, Tyr, Asp or Ala); Xaa at res. 83=(Leu, Tyr, Lys or Ile); Xaa at res. 84=(Lys, Arg, Asn, Tyr, Phe, Thr, Glu or Gly); Xaa at res. 85=(Lys, Arg, His, Gln, Asn, Glu or Val); Xaa at res. 86=(Tyr, His, Glu or Ile); Xaa at res. 87=(Arg, Glu, Gln, Pro or Lys); Xaa at res. 88=(Asn, Asp, Ala, Glu, Gly or Lys); Xaa at res. 89=(Met or Ala); Xaa at res. 90=(Val, Ile, Ala, Thr, Ser or Lys); Xaa at res. 91=(Val or Ala); Xaa at res. 92=(Arg, Lys, Gln, Asp, Glu, Val, Ala, Ser or Thr); Xaa at res. 93=(Ala, Ser, Glu, Gly, Arg or Thr); Xaa at res. 95=(Gly, Ala or Thr); Xaa at res. 97=(His, Arg, Gly, Leu or Ser). Further, after res. 53 in rBMP-3b and mGDF-10 there is an Ile; after res. 54 in GDF-1 there is a T; after res. 54 in BMP-3 there is a V; after res. 78 in BMP-8 and Dorsalin there is a G; after res. 37 in hGDF-1 there is Pro, Gly, Gly, Pro.

Generic Sequence 10 (SEQ ID NO: 7) includes all of Generic Sequence 9 (SEQ ID NO: 6) and in addition includes the following sequence (SEQ ID NO: 9) at its N-terminus:

```
            SEQ ID NO: 9
        Cys Xaa Xaa Xaa Xaa
         1                5
```

Accordingly, beginning with residue 6, each "Xaa" in Generic Sequence 10 is a specified amino acid defined as for Generic Sequence 9, with the distinction that each residue number described for Generic Sequence 9 is shifted by five in Generic Sequence 10. Thus, "Xaa at res. 1=(Tyr, Phe, His, Arg, Thr, Lys, Gln, Val or Glu)" in Generic Sequence 9 refers to Xaa at res. 6 in Generic Sequence 10. In Generic Sequence 10, Xaa at res. 2=(Lys, Arg, Gln, Ser, His, Glu, Ala, or Cys); Xaa at res. 3=(Lys, Arg, Met, Lys, Thr, Leu, Tyr, or Ala); Xaa at res. 4=(His, Gln, Arg, Lys, Thr, Leu, Val, Pro, or Tyr); and Xaa at res. 5=(Gln, Thr, His, Arg, Pro, Ser, Ala, Gln, Asn, Tyr, Lys, Asp, or Leu).

Based upon alignment of the naturally occurring morphogens within the definition of Generic Sequence 10, it should be clear that gaps and/or insertions of one or more amino acid residues can be tolerated (without abrogating biological activity) at least between or involving residues 11–12, 42–43, 59–60, 68–69 and 83–84.

As noted above, certain currently preferred morphogenic polypeptide sequences useful in this invention have greater than 60% identity, preferably greater than 65% identity, with the amino acid sequence defining the preferred reference sequence of hOP-1. These particularly preferred sequences include allelic and phylogenetic counterpart variants of the OP-1 and OP-2 proteins, including the Drosophila 60A protein, as well as the closely related proteins BMP-5, BMP-6 and Vgr-1. Accordingly, in certain particularly preferred embodiments, useful morphogenic proteins include active proteins comprising pairs of polypeptide chains within the generic amino acid sequence herein referred to as "OPX" (SEQ ID NO: 3), which defines the seven cysteine skeleton and accommodates the homologies between several identified variants of OP-1 and OP-2. Accordingly, each "Xaa" at a given position in OPX independently is selected from the residues occurring at the corresponding position in the C-terminal sequence of mouse or human OP-1 or OP-2. Specifically, each "Xaa" is independently selected from a group of one or more specified amino acids as defined below:

wherein Xaa at res. 2=(Lys or Arg); Xaa at res. 3=(Lys or Arg); Xaa at res. 11=(Arg or Gln); Xaa at res. 16=(Gln or Leu); Xaa at res. 19=(Ile or Val); Xaa at res. 23=(Glu or Gln); Xaa at res. 26=(Ala or Ser); Xaa at res. 35=(Ala or Ser); Xaa at res. 39=(Asn or Asp); Xaa at res. 41=(Tyr or Cys); Xaa at res. 50=(Val or Leu); Xaa at res. 52=(Ser or Thr); Xaa at res. 56=(Phe or Leu); Xaa at res. 57=(Ile or Met); Xaa at res. 58=(Asn or Lys); Xaa at res. 60=(Glu, Asp or Asn); Xaa at res. 61=(Thr, Ala or Val); Xaa at res. 65=(Pro or Ala); Xaa at res. 71=(Gln or Lys); Xaa at res. 73=(Asn or Ser); Xaa at res. 75=(Ile or Thr); Xaa at res. 80=(Phe or Tyr); Xaa at res. 82=(Asp or Ser); Xaa at res. 84=(Ser or Asn); Xaa at res. 89=(Lys or Arg); Xaa at res. 91=(Tyr or His); and Xaa at res. 97=(Arg or Lys).

In still another preferred embodiment, useful morphogenically active proteins have polypeptide chains with amino acid sequences comprising a sequence encoded by a nucleic acid that hybridizes, under low, medium or high stringency hybridization conditions, to DNA or RNA encoding reference morphogen sequences, e.g., C-terminal sequences defining the conserved seven cysteine domains of OP-1, OP-2, BMP-2, BMP-4, BMP-5, BMP-6, 60A, GDF-3, GDF-5, GDF-6, GDF-7 and the like. As used herein, high stringency hybridization conditions are defined as hybridization according to known techniques in 40% formamide, 5 X SSPE, 5 X Denhardt's Solution, and 0.1% SDS at 37° C. overnight, and washing in 0.1 X SSPE, 0.1% SDS at 50° C. Standard stringency conditions are well characterized in standard molecular biology cloning texts. See, for example, *Molecular Cloning A Laboratory Manual*, 2nd Ed., ed. by Sambrook, Fritsch and Maniatis (Cold Spring Harbor Laboratory Press: 1989); DNA Cloning, Volumes I and II (D. N. Glover ed., 1985); *Oligonucleotide Synthesis* (M. J. Gait ed., 1984): *Nucleic Acid Hybridization* (B. D. Hames & S. J. Higgins eds. 1984); and B. Perbal, *A Practical Guide To Molecular Cloning* (1984).

Accordingly, the morphogenic proteins useful in the materials and methods of this invention can include proteins comprising any of the polypeptide chains described above, whether isolated from naturally-occurring sources, or produced by recombinant DNA or other synthetic techniques, and includes allelic and phylogenetic counterpart variants of these proteins, as well as biosynthetic variants (muteins) thereof, and various truncated and fusion constructs. Deletion or addition mutants also are envisioned to be active, including those which may alter the conserved C-terminal six or seven cysteine domain, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms

```
Cys Xaa Xaa His Glu Leu Tyr Val Ser Phe Xaa Asp Leu Gly Trp Xaa Asp Trp
 1           5                  10                  15
Xaa Ile Ala Pro Xaa Gly Tyr Xaa Ala Tyr Tyr Cys Glu Gly Glu Cys Xaa Phe Pro
    20              25                  30                      35
Leu Xaa Ser Xaa Met Asn Ala Thr Asn His Ala Ile Xaa Gln Xaa Leu Val His Xaa
        40              45                  50              55
Xaa Xaa Pro Xaa Xaa Val Pro Lys Xaa Cys Cys Ala Pro Thr Xaa Leu Xaa Ala
            60              65                  70
Xaa Ser Val Leu Tyr Xaa Asp Xaa Ser Xaa Asn Val Ile Leu Xaa Lys Xaa Arg
75              80              85                  90
Asn Met Val Val Xaa Ala Cys Gly Cys His
            95              100
``` of native or biosynthetic proteins, produced by expression of recombinant DNA in host cells.

The bone morphogenic proteins contemplated herein can be expressed from intact or truncated cDNA or from synthetic DNAs in prokaryotic or eukaryotic host cells, and purified, cleaved, refolded, and dimerized to form morphogenically active compositions. Currently preferred host cells include, without limitation, prokaryotes, including *E. coli*, and eukaryotes, including yeast, and mammalian cells, such as CHO, COS or BSC cells. One of ordinary skill in the art will appreciate that other host cells can be used to advantage. Detailed descriptions of the morphogenic proteins useful in the practice of this invention, including how to make, use and test them for activity, are disclosed in numerous publications, including those recited herein, the disclosures of which are incorporated by reference herein. Accordingly, using standard molecular biology texts and procedures, and the knowledge available in the art, the skilled genetic engineer/molecular biologist can isolate genes from cDNA or genomic libraries of various different biological species, which encode appropriate amino acid sequences, or construct DNAs from oligonucleotides, and then can express them in various types of host cells, including both prokaryotes and eukaryotes, to produce large quantities of active proteins capable of stimulating neural tissue morphogenesis in a mammal.

In other embodiments, as an alternative to the administration of a morphogenic protein, an effective amount of an agent competent to stimulate or induce increased endogenous morphogen expression in a mammal may be administered by any of the routes described herein. Such an inducer of a morphogen may be provided to a mammal, e.g., by systemic administration to the mammal or by direct administration to the neural tissue. A method for identifying and testing inducers (stimulating agents) competent to modulate the levels of endogenous morphogens in a given tissue is described in detail in published applications WO 93/05172 and WO 93/05751, the teachings of which are incorporated herein by reference. Briefly, candidate compounds can be identified and tested by incubation in vitro with a test tissue or cells thereof, or a cultured cell line derived therefrom, for a time sufficient to allow the compound to affect the production, i.e., the expression and/or secretion, of a morphogen produced by the cells of that tissue. Suitable tissue, or cultured cells of a suitable tissue, preferably can be selected from renal epithelium, ovarian tissue, fibroblasts, and osteoblasts.

In yet other embodiments, an agent which acts as an agonist of a morphogen receptor may be administered instead of the morphogen itself. Such an agent may also be referred to an a morphogen "mimic," "mimetic," or "analog." Thus, for example, a small peptide or other molecule which can mimic the activity of a morphogen in binding to and activating the morphogen's receptor may be employed as an equivalent of the morphogen. Preferably the agonist is a full agonist, but partial morphogen receptor agonists may also be advantageously employed. Methods of identifying such agonists are known in the art and include assays for compounds which induce morphogen-mediated responses (e.g, induction of differentiation of metanephric mesenchyme, induction of endochondral bone formation). For example, methods of identifying morphogen inducers or agonists of morphogen receptors may be found in U.S. application Ser. No. 08/478,097 filed Jun. 7, 1995 and U.S. application Ser. No. 08/507,598 filed Jul. 26, 1995, the disclosures of which are incorporated herein by reference.

Finally, as described below, in other embodiments, cells may be implanted into the subject afflicted with an ischemic or traumatic injury of the central nervous system in order to serve as a source of morphogen and/or to provide a source of additional functional neural tissue. Such cells may be host or donor cells which normally express morphogens, which have been transformed so as to express morphogens, or which have been treated with morphogens to induce differentiation.

C. Mammals Eligible for Treatment

As a general matter, the methods of the present invention may be applied to the treatment of any mammalian subject afflicted with stroke or a traumatic injury of the central nervous system. The method can be practiced with mammals in whom the stroke or other traumatic injury arose at least 6 hours before the start of treatment, for example as twelve, twenty-four or forty-eight hours or longer before treatment. Practice of the invention confers a significant clinical benefit on the afflicted mammal, in that the invention beneficially confers a detectable, clinically significant restoration of a central nervous system function as defined herein. The invention is suitable for the treatment of any primate, preferably a higher primate such as a human. In addition, however, the invention may be employed in the treatment of domesticated mammals which are maintained as human companions (e.g., dogs, cats, horses), which have significant commercial value (e.g., goats, pigs, sheep, cattle, sporting or draft animals), which have significant scientific value (e.g., captive or free specimens of endangered species, or inbred or engineered animal strains), or which otherwise have value. One of ordinary skill in the medical or veterinary arts is trained to recognize whether a mammal is afflicted with an ischemic or traumatic injury of the central nervous system. For example, routine testing and/or clinical or veterinary diagnostic evaluation will reveal whether the mammal has acquired an impairment or loss of central nervous system (e.g., neurologic) function. Clinical and non-clinical indications, as well as accumulated experience, relating to the presently disclosed and other methods of treatment, should appropriately inform the skilled practitioner in deciding whether a given individual is afflicted with an ischemic or traumatic injury of the central nervous system and whether any particular treatment is best suited to the subject's needs, including treatment according to the present invention.

D. Formulations and Methods of Treatment

The morphogens, morphogen inducers, or agonists of morphogen receptors of the present invention may be administered by any route which is compatible with the particular morphogen, inducer, or agonist employed. Thus, as appropriate, administration may be oral or parenteral, including intravenous and intraperitoneal routes of administration. In addition, administration may be by periodic injections of a bolus of the morphogen, inducer or agonist, or may be made more continuous by intravenous or intraperitoneal administration from a reservoir which is external (e.g., an i.v. bag) or internal (e.g., a bioerodable implant, or a colony of implanted, morphogen-producing cells).

The therapeutic agents of the invention (i.e., morphogens, morphogen inducers or agonists of morphogen receptors) may be provided to an individual by any suitable means, directly (e.g., locally, as by injection, implantation or topical administration to a tissue locus) or systemically (e.g., parenterally or orally). Where the agent is to be provided parenterally, such as by intravenous, subcutaneous, intramolecular, ophthalmic, intraperitoneal, intramuscular, buccal, rectal, vaginal, intraorbital, intracerebral, intracranial, intraspinal, intraventricular, intrathecal, intracisternal, intracapsular, intranasal or by aerosol administration the agent preferably comprises part of an aqueous solution. The solution is physiologically acceptable so that in addition to delivery of the desired agent to the patient, the solution does not otherwise adversely affect the patient's electrolyte and/or volume balance. The aqueous medium for the agent thus can comprise normal physiologic saline (e.g., 9.85% NaCl, 0.15M, pH 7–7.4).

If desired, a given morphogen or other agent may be made more soluble by association with a suitable molecule. For example, association of the mature morphogen dimer with the pro domain results in the pro form of the morphogen which typically is more soluble or dispersible in physiological solutions than the corresponding mature form. In fact, endogenous morphogens are thought to be transported (e.g., secreted and circulated) in the mammalian body in this form. This soluble form of the protein can be obtained from culture medium of morphogen-secreting mammalian cells, e.g., cells transfected with nucleic acid encoding and competent to express the morphogen. Alternatively, a soluble species can be formulated by complexing the mature, morphogenically active polypeptide dimer (or an active fragment thereof) with a morphogen pro domain or a solubility-enhancing fragment thereof. Solubility-enhancing pro domain fragments can be any N-terminal, C-terminal or internal fragment of the pro region of a member of the morphogen family that complexes with the mature polypeptide dimer to enhance stability and/or dissolubility of the resulting noncovalent or convalent complex. Typically, useful fragments are those cleaved at the proteolytic site Arg-Xaa-Xaa-Arg. A detailed description of soluble complex forms of morphogenic proteins, including how to make, test and use them, is described in WO 94/03600 (PCT/US93/07189). In the case of OP-1, useful pro domain fragments include the intact pro domain (residues 30–292) and fragments 48–292 or 158–292, all of Se. ID No. 5. Another molecule capable of enhancing solubility and particularly useful for oral administrations, is casein. For example, addition of 0.2% casein increases solubility of the mature active form of OP-1 by 80%. Other components found in milk and/or various serum proteins also may be useful.

Useful solutions for parenteral administration may be prepared by any of the methods well known in the pharmaceutical art, described, for example, in *Remington's Pharmaceutical Sciences* (Gennaro, A., ed.), Mack Pub., 1990. Formulations of the therapeutic agents of the invention may include, for example, polyalkylene glycols such as polyethylene glycol, oils of vegetable origin, hydrogenated naphthalenes, and the like. Formulations for direct administration, in particular, may include glycerol and other compositions of high viscosity to help maintain the agent at the desired locus. Biocompatible, preferably bioresorbable, polymers, including, for example, hyaluronic acid, collagen, tricalcium phosphate, polybutyrate, lactide, and glycolide polymers and lactide/glycolide copolymers, may be useful excipients to control the release of the agent in vivo. Other potentially useful parenteral delivery systems for these agents include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or cutric acid for vaginal administration. Suppositories for rectal administration also may be prepared by mixing the morphogen, inducer or agonist with a non-irritating excipient such as cocoa butter or other compositions which are solid at room temperature and liquid at body temperatures.

Formulations for topical administration to the skin surface may be prepared by dispersing the morphogen, inducer or agonist with a dermatologically acceptable carrier such as a lotion, cream, ointment or soap. Particularly useful are carriers capable of forming a film or layer over the skin to localize application and inhibit removal. For topical administration to internal tissue surfaces, the agent may be dispersed in a liquid tissue adhesive or other substance known to enhance adsorption to a tissue surface. For example, hydroxypropylcellulose or fibrinogen/thrombin solutions may be used to advantage. Alternatively, tissue-coating solutions, such as pectin-containing formulations may be used.

Alternatively, the agents described herein may be administered orally. Oral administration of proteins as therapeutics generally is not practiced as most proteins are readily degraded by digestive enzymes and acids in the mammalian digestive system before they can be absorbed into the bloodstream. However, the morphogens described herein typically are acid stable and protease-resistant (see, for example, U.S. Pat. No. 4,968,590). In addition, at least one morphogen, OP-1, has been identified in mammary gland extract, colostrum and 57-day milk. Moreover, the OP-1 purified from mammary gland extract is morphogenically active and also is detected in the bloodstream. Maternal administration, via ingested milk, may be a natural delivery route of TGF-β superfamily proteins. Letterio, et al. (1994), *Science* 264: 1936–1938, report that TGF-β is present in murine milk, and that radiolabelled TGF-β is absorbed by gastrointestinal mucosa of suckling juveniles. Labeled, ingested TGF-β appears rapidly in intact form in the juveniles' body tissues, including lung, heart and liver. Finally, soluble form morphogen, e.g., mature morphogen associated with the pro domain, is morphogenically active. These findings, as well as those disclosed in the examples below, indicate that oral and parenteral administration are viable means for administering TGF-β superfamily proteins, including the morphogens, to an individual. In addition, while the mature forms of certain morphogens described herein typically are sparingly soluble, the morphogen form found in milk (and mammary gland extract and colostrum) is readily soluble, probably by association of the mature, morphogenically active form with part or all of the pro domain of the expressed, full length polypeptide sequence and/or by association with one or more milk components. Accordingly, the compounds provided herein also may be associated with molecules capable of enhancing their solubility in vitro or in vivo.

The compounds provided herein also may be associated with molecules capable of targeting the morphogen, inducer or agonist to the desired tissue. For example, an antibody, antibody fragment, or other binding protein that interacts specifically with a surface molecule on cells of the desired tissue, may be used. Useful targeting molecules may be designed, for example, using the single chain binding site technology disclosed, for example, in U.S. Pat. No. 5,091,513. Targeting molecules can be covalently or non-covalently associated with the morphogen, inducer or agonist.

As will be appreciated by one of ordinary skill in the art, the formulated compositions contain therapeutically-effective amounts of the morphogen, morphogen inducers or agonists of morphogen receptors. That is, they contain an amount which provides appropriate concentrations of the agent to the affected nervous system tissue for a time sufficient to stimulate a detectable restoration of central nervous system function, up to and including a complete restoration thereof. As will be appreciated by those skilled in the art, these concentrations will vary depending upon a number of factors, including the biological efficacy of the selected agent, the chemical characteristics (e.g., hydrophobicity) of the specific agent, the formulation thereof, including a mixture with one or more excipients, the administration route, and the treatment envisioned, including whether the active ingredient will be administered directly into a tissue site, or whether it will be administered systemically. The preferred dosage to be administered also is likely to depend on such variables such as the condition of the diseased or damaged tissues, and the overall health status of the particular mammal. As a general matter, single, daily, biweekly or weekly dosages of 0.00001–1000 mg of a morphogen are sufficient with 0.0001–100 mg being preferable, and 0.001 to 10 mg being even more preferable. Alternatively, a single, daily, biweekly or weekly dosage of 0.01–1000 µg/kg body weight, more preferably 0.01–10 mg/kg body weight, may be advantageously employed. The present effective dose can be administered in a single dose or in a plurality (two or more) of installment doses, as desired or considered appropriate under the specific circumstances. A bolus injection or diffusable infusion formulation can be used. If desired to facilitate repeated or frequent infusions, implantation of a semi-permanent stent (e.g., intravenous, intraperitoneal, intracisternal or intracapsular) may be advisable. In Example 2 below, intracisternal administration of 6–240 kg/kg of the reference morphogen (hOP-1) conferred clearly detectable levels of restoration of lost or impaired central nervous system function. It should be noted that no obvious morphogen induced pathological lesions arise when mature morphogen (e.g., OP-1, 20 mg) is administered daily to normal growing rats for 21 consecutive days. Moreover, 10 mg systemic injections of morphogen (e.g., OP-1) injected daily for 10 days into normal newborn mice does not produce any gross abnormalities.

The morphogens, inducers or agonists of the invention may, of course, be administered alone or in combination with other molecules known to be beneficial in the treatment of the conditions described herein. For example, various well-known growth factors, hormones, enzymes, therapeutic compositions, antibiotics, or other bioactive agents can also be administered with the morphogen. Thus, various known growth factors such as NGF, EGF, PDGF, IGF, FGF, TGF-α, and TGF-β, as well as enzymes, enzyme inhibitors, antioxidants, anti-inflammatory agents, free radical scavenging agents, antibiotics and/or chemoattractant/chemotactic factors, can be included in the present administratable morphogen formulation. To facilitate uptake by central nervous system tissue, the morphogens, inducers or agonists provided herein can be derivatized or conjugated to a lipophilic moiety or to a substance that is actively transported across the blood-brain barrier.

Practice of the invention, including additional preferred aspects and embodiments thereof, will be still more fully understood from the following examples, which are presented herein for illustration only and should not be construed as limiting the invention in any way.

EXAMPLE 1

Preparation of Soluble Morphogen Protein Solutions for In Vivo Administration

A. Aqueous Solutions

While the mature dimeric morphogenic proteins defined herein typically are substantially only sparingly soluble in physiological buffers, they can be solubilized to form injectable solutions. One exemplary aqueous solution containing a morphogen can be made, for example, by dissolving or dispersing the morphogen in 50% ethanol containing acetonitrile in 0.1% trifluoroacetic acid (TFA) or 0.1% HCl, or in an equivalent solvent. One volume of the resultant solution then is added, for example, to ten volumes of phosphate buffered saline (PBS), which further may include 0.1–0.2% human serum albumin (HSA) or a similar carrier protein. The resultant solution preferably is vortexed extensively to produce a physiologically acceptable morphogen formulation.

In another embodiment, the morphogen, including OP-1, can be solubilized by reducing the pH of the solution. In one currently preferred formulation, the protein is solubilized in 0.2 mM acetate buffer, pH 4.5, containing 5% mannitol, to render the solution more isotonic. Other standard means for creating physiologically acceptable formulations are contemplated to be within the skill of the art.

B. Soluble Complex Formulations

Another currently preferred form of the morphogen useful herein, having improved solubility in aqueous solutions, is a dimeric morphogenic protein comprising at least the C-terminal seven cysteine domain characteristic of the morphogen family, complexed with a peptide comprising a pro region of a member of the morphogen family, or a solubility-enhancing fragment thereof, or an allelic, species or other sequence variant thereof. Solubility-enhancing fragment can be any N-terminal or C-terminal fragment of the pro region of a member of the morphogen family that complexes with the mature polypeptide dimer to enhance the stability of the soluble complex. Preferably, the dimeric morphogenic protein is complexed with two pro region peptides.

As described above and in published application WO 94/03600, the teachings of which are incorporated herein by reference, the soluble complex form can be isolated from the cell culture media (or a body fluid) under appropriate conditions. Alternatively, the complex can be formulated in vitro.

Soluble morphogen complexes can be isolated from conditioned media using a simple, three step chromatographic protocol performed in the absence of denaturants. The protocol involves running the media (or body fluid) over an affinity column, followed by ion exchange and gel filtration chromatographies generally as described in WO 94/03600. The affinity column described below is a Zn-IMAC column. The example used OP-1 and is not intended to be limiting. The present protocol has general applicability to the purification of a variety of morphogens, all of which are anticipated to be isolatable using only minor modifications of the protocol described below. An alternative protocol also envisioned to have utility includes an immunoaffinity column, created using standard procedures and, for example, using antibody specific for a given morphogen pro domain (complexed, for example, to a protein A-conjugated Sepharose column). Protocols for developing immunoaffinity columns are well described in the art (see, for example, *Guide to Protein Purification, M.* Deutscher, ed., Academic Press, San Diego, 1990, particularly sections VII and XI thereof).

In this example, OP-1 was expressed in mammalian (CHO, Chinese hamster ovary) cells as described in the art (see, for example, international application U.S. application Ser. No. 90/05903 (WO 91/05802). The CHO cell conditioned media containing 0.5% FBS is initially purified using Immobilized Metal-Ion Affinity Chromatography (IMAC). The soluble OP-1 complex from conditioned media binds very selectively to the Zn-IMAC resin and a high concentration of imidazole (50 mM imidazole, pH 8.0) is required for the effective elution of the bound complex. The Zn-IMAC purified soluble OP-1 is next applied to an S-Sepharose action-exchange column equilibrated in 20 mM $NaPO_4$ (pH 7.0) with 50 mM NaCl. The protein then is applied to a Sephacryl S-200HR column equilibrated in TBS. Using substantially the same protocol, soluble morphogens also can be isolated from one or more body fluids, including serum, cerebrospinal fluid or peritoneal fluid.

The soluble OP-1 complex elutes with an apparent molecular weight of 110 kDa. This agrees well with the predicted composition of the soluble OP-1 complex with one mature OP-1 dimer (35–36 kDa) associated with two pro-domains (39 kDa each). Purity of the final complex can be verified by running the appropriate fraction in a reduced 15% polyacrylamide gel.

As an alternative to purifying soluble complexes from culture media or a body fluid, soluble complexes can be formulated from purified pro domains and mature dimeric species. Successful complex formation apparently requires association of the components under denaturing conditions sufficient to relax the folded structure of these molecules, without affecting disulfide bonds. Preferably, the denaturing conditions mimic the environment of an intracellular vesicle sufficiently such that the cleaved pro domain has an opportunity to associate with the mature dimeric species under relaxed folding conditions. The concentration of denaturant in the solution then is decreased in a controlled, preferably step-wise manner, so as to allow proper refolding of the dimer and pro regions while maintaining the association of the pro domain with the dimer. Useful denaturants include 4–6M urea or guanidine hydrochloride (GuHCl), in buffered solutions of pH 4–10, preferably pH 6–8. The soluble complex then is formed by controlled dialysis or dilution into a solution having a final denaturant concentration of less than 0.1–2M urea or GuHCl, preferably 1–2 M urea of GuHCl, which then preferably can be diluted into a physiological buffer. Protein purification/renaturing procedures and considerations are well described in the art, and details for developing a suitable renaturing protocol readily can be determined by one having ordinary skill in the art. One useful text on the subject is *Guide to Protein Purification*, M. Deutscher, ed., Academic Press, San Diego, 1990, particularly section V. Complex formation also may be aided by addition of one or more chaperone proteins.

The stability of the highly purified soluble morphogen complex in a physiological buffer, e.g., Tris-buffered saline (TBS) and phosphate-buffered saline (PBS), can be enhanced by any of a number of means, including any one or more of three classes of additives. These additives include basic amino acids (e.g., L-arginine, lysine and betaine); nonionic detergents (e.g, Tween 80 or Nonidet P-120); and carrier proteins (e.g., serum albumin and casein). Useful concentrations of these additives include 1–100 mM, preferably 10–70 mM, including 50 mM, basic amino acid;, 0.01–1.0%, preferably 0.05–0.2%, including 0.1% (v/v) nonionic detergent;, and 0.01–1.0%, preferably 0.05–0.2%, including 0. 1% (w/v) carrier protein.

EXAMPLE 2

Stroke Model Involving Surgical Occlusion of the Cerebral Artery

The middle cerebral artery (MCA) occlusion model is a well accepted model of a focal ischemic episode or stroke (Gotti, et al., (1990) *Brain Res.* 522: 290–307). Focal ischemia is produced by obstructing blood flow through the MCA, resulting in infarction of the brain locus supplied by this artery. The MCA model is reasonably predictive of the ability and efficacy of drugs, such as morphogen, to alter functional recovery in humans in whom central nervous system tissue has been damaged or lost due to stroke. For example, the MCA model is deemed reasonably predictive of drug efficacy to restore or detectably improve motor coordination, sensory perception, speech or any other central nervous system function naturally contributed to by tissue within the territory of the MCA.

Animals that were treated with OP-1, beginning 24 hours after occlusion of the MCA, performed significantly better than vehicle-treated animals in a variety of functional/behavioral tests as described below.

I. Surgical Occlusion Procedure

The animals used in this study were male Sprague-Dawley rats weighing 250–300 grams (Charles River). For surgical procedures, the animals were anesthetized with 2% halothane in 70% $NO_2$/30% $O_2$. The tail artery was cannulated in order to monitor blood gases and blood glucose. Body temperature was monitored using a rectal probe and was maintained at 37±0.5° C. with a heating pad. The proximal right middle cerebral artery (MCA) was occluded permanently using a modification of the method of Tamura, et al. (1981, *J. Cereb. Blood Flow Metab.* 1: 53–60). Briefly, the proximal MCA was exposed transcranially without removing the zygomatic arch or transacting the facial nerve. The artery was then electrocoagulated using a bipolar microcoagulator from just proximal to the olfactory tract to the inferior cerebral vein, and was then transected (Bederson, et al., (1986) *Stroke* 17: 472–476). Rats were observed until they regained consciousness and were then returned to their home cages. Cefazolin sodium (40 mg/kg, i.p.), an antibiotic, was administered to all animals on the day before and just after stroke surgery in order to prevent infection. During stroke surgery, there were no differences in the levels of blood gases or glucose among animals that subsequently received OP-1 or vehicle treatment.

II. Administration of Morphogen

Animals in the treatment group received OP-1 intracisternally at a dose of 1 or 10 μg/injection. Control animals received vehicle solutions lacking OP-1 but with all other components at equivalent final concentrations.

To administer the injection, the animals were anesthetized with halothane in 70% $NO_2$/30% $O_2$ and placed in a stereotaxic frame. The procedure for intracisternal injection of OP-1 containing solutions or vehicle-only solutions was identical. Using aseptic technique, OP-1 (1 or 10 μg/injection) or an equivalent volume of vehicle were introduced by percutaneous injection (10 μl/injection) into the cisterna magna using a Hamilton syringe fitted with a 26 gauge needle (Yamada, et al., (1991) *J. Cereb. Blood Flow Metab.* 11: 472–478). Before each injection, 1–2 μl of cerebrospinal fluid (CSF) was drawn back through the Hamilton syringe to verify needle placement in the subarachnoid space. Preliminary studies demonstrated that a dye, 1% Evans blue, delivered in this fashion diffused freely through the basal cisterns and over the cerebral cortex within one hour of injection. Animals were randomly assigned to either of the OP-1 treatment groups or to the vehicle treatment group.

In a first study, intracisternal injections (10 μg/injection OP-1 or vehicle) were made biweekly for four weeks, starting 24 hours after stroke (i.e., on post-stroke days 1, 4, 8, 11, 15, 18, 22, and 25). In a second study, animals received two intracisternal injections (2×1 µg/injection OP-1, 2×10 µg/injection OP-1, or 2×vehicle); the first injection was administered 24 hours after stroke and the second injection was administered 4 days after stroke. In a third study, a single injection (10 µg/injection OP-1 or vehicle) was administered 24 hours after stroke.

III. Behavioral Testing

To accustom the animals to handling, which would be necessary for behavioral/functional testing, they were handled for three days before surgery; for 10 minutes each day. Following surgery, they were housed in individual cages. Four standard functional/behavioral tests were used to assess sensorimotor and reflex function after infarction. The tests have been fully described in the literature, including Bederson, et al., (1986) *Stroke* 17: 472–476; DeRyck, et al., (1992) *Brain Res*. 573: 44–60; Markgraf, et al., (1992) *Brain Res*. 575: 238–246; and Alexis, et al., (1995) *Stroke* 26: 2338–2346.

A. The Forelimb Placing Test

Briefly, the forelimb placing test is comprised of three subtests. Separate scores are obtained for each forelimb. For the visual placing subtest, the animal is held upright by the researcher and brought close to a table top. Normal placing of the limb on the table is scored as "0," delayed placing (<2 sec) is scored as "1," and no or very delayed placing (>2 sec) is scored as "2." Separate scores are obtained first as the animal is brought forward and then again as the animal is brought sideways to the table (maximum score per limb=4; in each case higher numbers denote greater deficits). For the tactile placing subtest, the animal is held so that it cannot see or touch the table top with its whiskers. The dorsal forepaw is touched lightly to the table top as the animal is first brought forward and then brought sideways to the table. Placing each time is scored as above (maximum score per limb=4). For the proprioceptive placing subtest, the animal is brought forward only and greater pressure is applied to the dorsal forepaw; placing is scored as above (maximum score per limb=2). These subscores are added to give the total forelimb placing score per limb (range=010). In some animals, the whisker placing subtest was done, in which the ability of the animal to place the forelimb in response to whisker stimulation by the tabletop was tested (maximum score per limb=2). Then subscores were added to give the total forelimb placing score per limb (range=0–10, 0–12 with whisker subtest.

B. The Hindlimb Placing Test

The hindlimb placing test is conducted in the same manner as the forelimb placing test but involves only tactile and proprioceptive subtests of the hindlimbs (maximal scores 4 and 2, respectively; total score range=0–6).

C. The Modified Balance Beam Test

The modified balance beam test examines vestibulo motor reflex activity as the animal balances on a narrow beam (30×1.3 cm) for 60 seconds. Ability to balance on the beam is scored as follows: 1-animal balances with all four paws on top of beam; 2-animal puts paws on side of beam or wavers on beam; 3-one or two limbs slip off beam; 4-three limbs slip off beam; 5-animal attempts to balance with paws on beam but falls off; 6-animal drapes over beam, then falls off; 7-animal falls off beam without an attempt to balance. Animals received three training trials before surgery: the score of the last of these was taken as the baseline score.

D. The Postural Reflex Test

The postural reflex test measures both reflex and sensorimotor function. Animals are first held by the tail suspended above the floor. Animals that reach symmetrically toward the floor with both forelimbs are scored "0." Animals showing abnormal postures (flexing of a limb, rotation of the body) are then placed on a plastic-backed sheet of paper. Those animals able to resist side-to-side movement with gentle lateral pressure are scored "1," while those unable to resist such movement are scored "2." All functional/behavioral tests were administered just before stroke surgery and then every other day from post-stroke day 1 to day 31. At each session, animals were allowed to adapt to the testing room for 30 minutes before testing was begun.

IV. Histological Analysis

On day 31 after MCA occlusion, animals were anesthetized deeply with pentobarbital and perfused transcardially with heparinized saline followed by 10% buffered formalin. Brains were removed, cut into three pieces, and stored in 10% buffered formalin before dehydration and embedding in paraffin. Coronal sections (5 µm) were cut on a sliding microtome, mounted onto glass slides, and stained with hematoxylin and eosin. The area of cerebral infarcts on each of seven slices (+4.7, +2.7, +0.7, −1.3, −3.3, −5.3, and −7.3 compared to bregma) was determined using a computer interfaced imaging system (Rioquant, R&M Biometnix, Inc., Nashville, Teen.). Total infarct area per slice was determined by the "indirect method" as [the area of the intact contralateral hemisphere]- [the area of the intact ipsilateral hemisphere] to correct for brain shrinkage during processing (Swanson, et al., (1990) *J. Cereb. Blood Flow Metab*. 10: 290–293). Infarct volume was then expressed as a percentage of the intact contralateral hemispheric volume. The volumes of infarction in cortex and striatum were also determined separately using these methods.

The practitioner performing intracisternal injections, behavioral testing, and histological analysis was blinded to the treatments assigned until all data had been collected. Data were expressed as means ±SD or means ±SEM and were analyzed by repeated measures analysis of variance (ANOVA) followed by appropriate unpaired two tailed tests, with the Bonferroni correction for multiple comparisons.

V. Results

Difference in Total Infarct Volume and Body Weight Between OP-1-treated or Vehicle-Treated Animals The right lateral cerebral cortex and underlying striatum of both OP-1 -treated animals and vehicle-treated animals showed large infarcts in the territory of the MCA. Brain regions severely damaged by infarcts included parietal cortex, areas 1 and 2 (Parl, Par2) and granular insular cortex (GI). Regions partially damaged by infarcts included frontal cortex, areas 1, 2, and 3 (FRI, FR2, FR3); a granular insular cortex (Al); temporal cortex, areas 1 and 3 (Tell, Tel3); lateral occipital cortex, area 2 (Oc2L); the cortical forelimb area (FL), and the caudoputamen (cPu; Paxinos and Watson, 1986). The cortical hindlimb area (HL) was generally spared by infarcts.

There was no difference in total infarct volume between animals treated with a series of OP-1 intracistemal administrations (8×10 µg /injection) and vehicle-treated animals (26.3±2.5% vs. 28.0±2.0% of intact contralateral hemispheric volume, respectively, t=0.538, p-n.s.). Moreover, there was no difference in cortical or striatal infarct volume among the OP-1-treated animals and the vehicle-treated animals, when these volumes were calculated separately (cortex: 30.9±3.1% vs. 31.9±2.9% of intact contralateral cortex volume, respectively, t=0.254, P-n.s.; striatum: 66.0±3.0% vs. 66.5±2.9% of intact contralateral striatum volume, respectively, t=0.121, p-n.s.). Further, inspection of hematoxylin and eosin-stained sections showed no evidence of abnormal cell proliferation in the brains of OP-1-treated animals. Similarly, the total infarct volume of animals receiving a single OP-1 injection or two OP-1 injections did not differ significantly from the corresponding vehicle-treated animals (data not shown).

Figure 4:
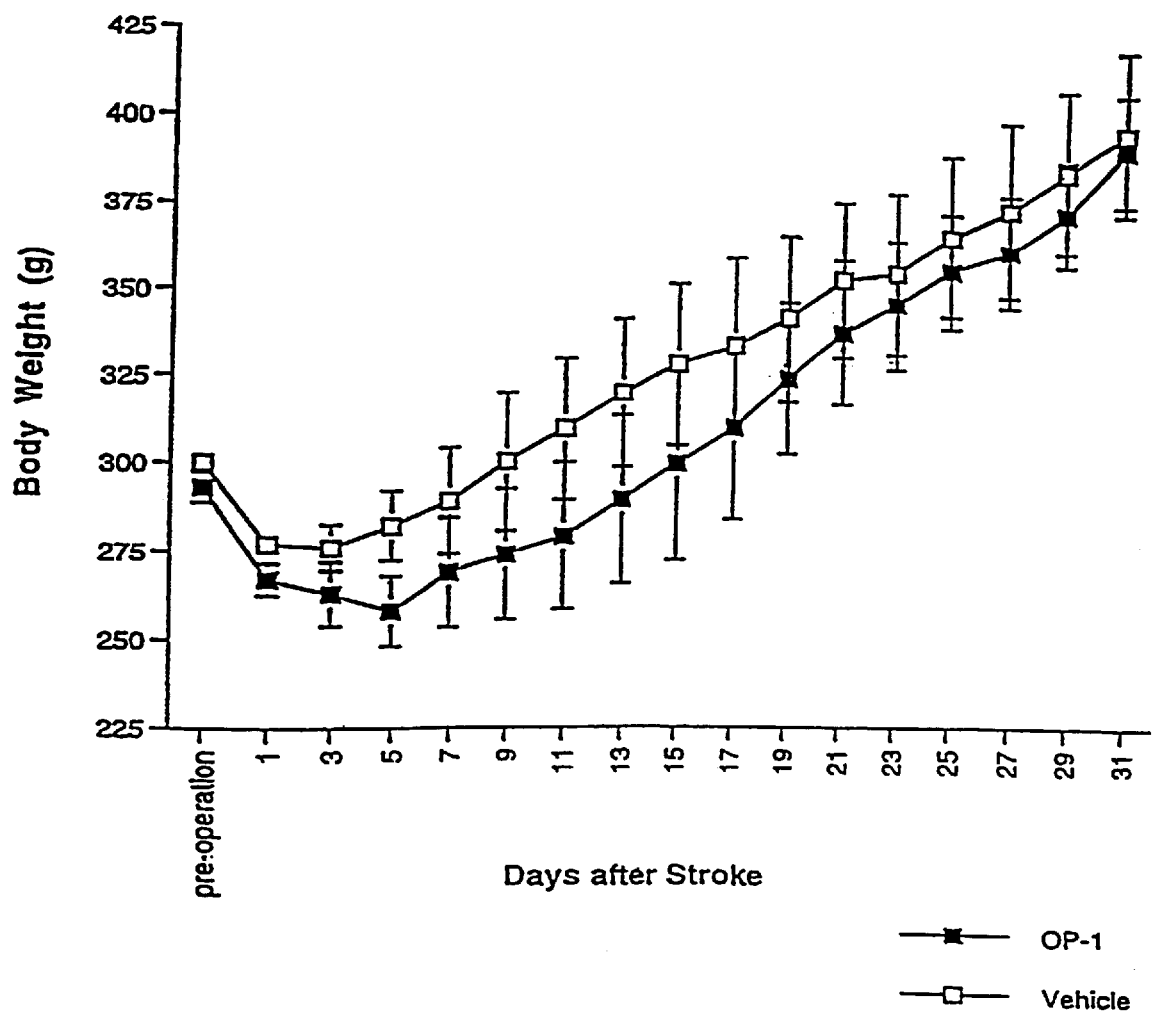
FIG. 4 is a line graph depicting body-weight of OP-1-treated animals (10 $\mu$g/intracisternal injection; total OP-1 delivered in 8 injections=80 $\mu$g/animal; N=7; solid squares) and vehicle-treated animals (N=7; open squares)
Figure 5A:
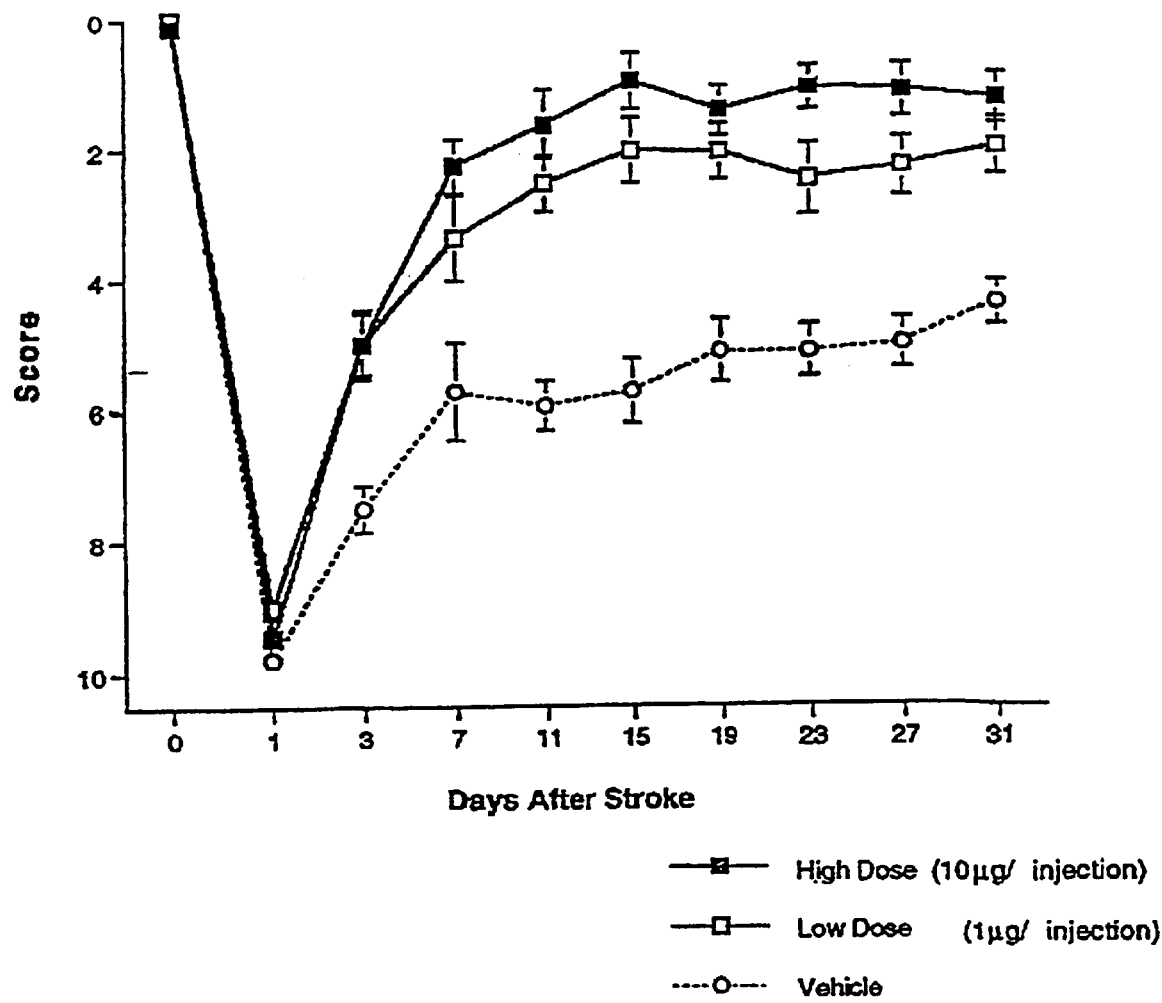
FIGS. 5A–5B are line graphs depicting forelimb placing scores without (5A) and with whisker placing (5B) of affected (left) limbs of High dose OP-1-treated animals (10 $\mu$g/intracisternal injection; total OP-1 delivered in 2 injections=20 $\mu$g/animal; N=9 animals; solid squares), Low dose OP-1-treated animals (1 $\mu$g/intracisternal injection; total OP-1 delivered in 2 injections=2 $\mu$g/animal; N=8 animals; open squares), and vehicle-treated animals (N=9, open circles)
Figure 5B:
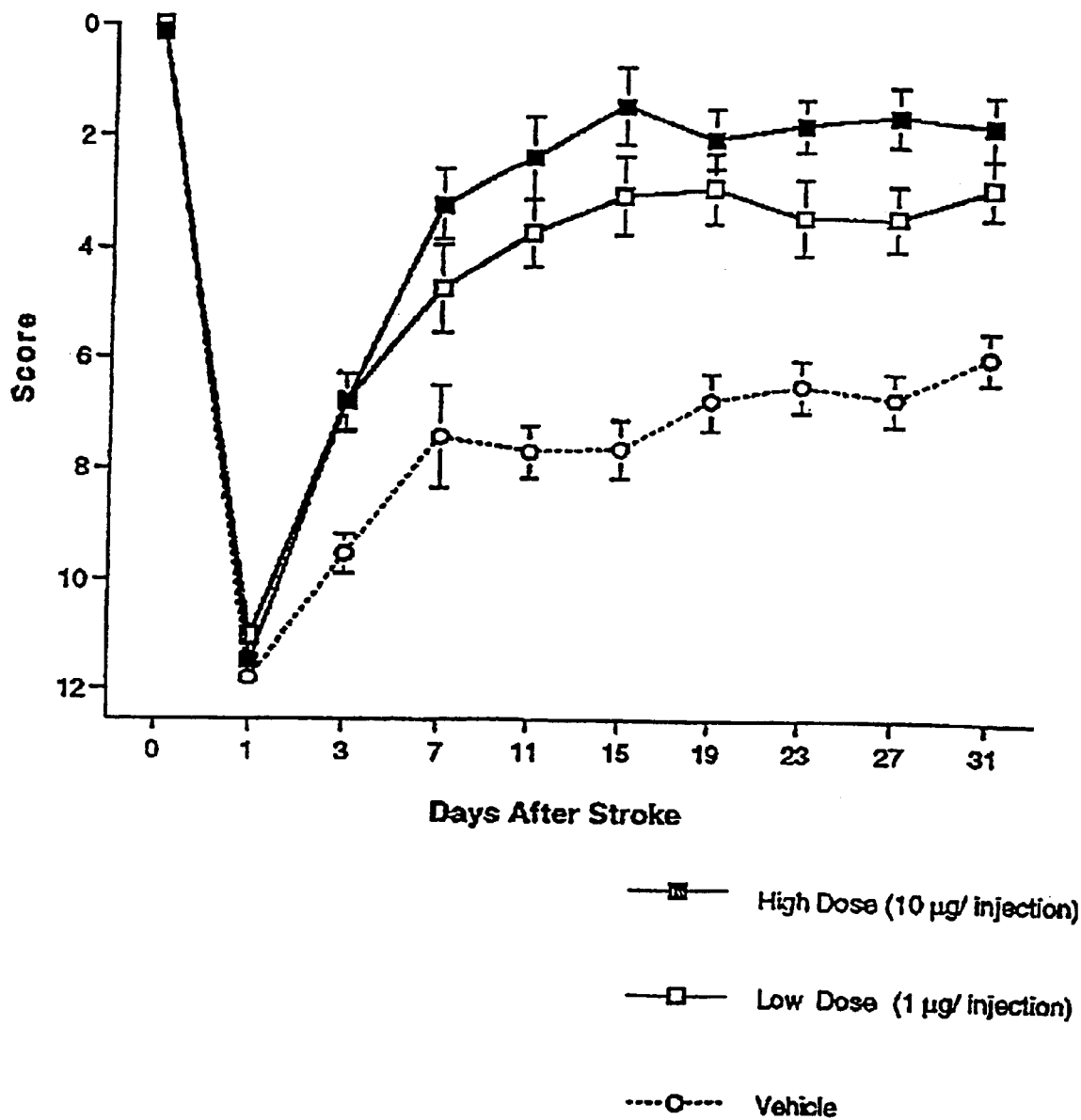
Figure 6:
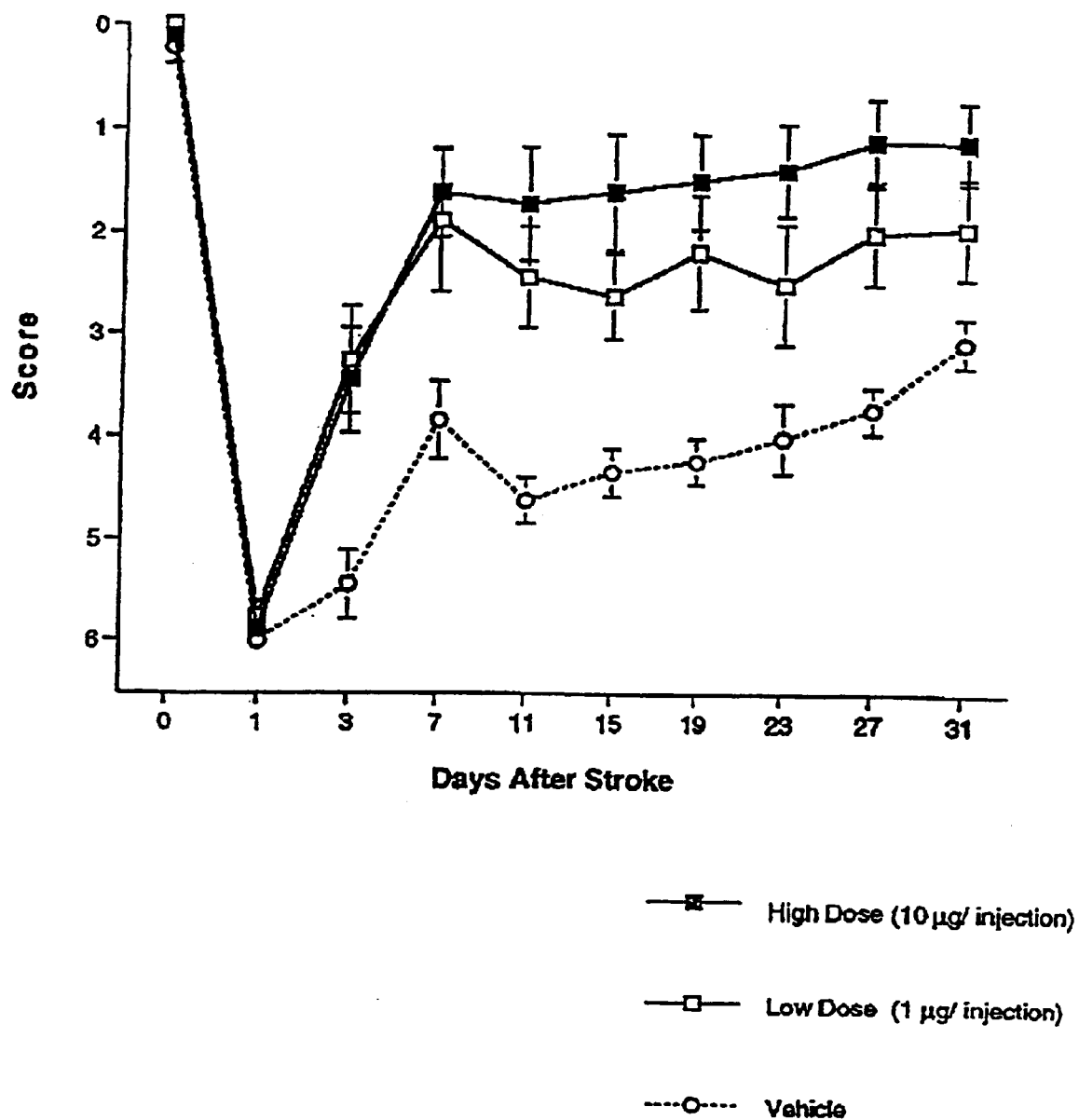
FIG. 6 is a line graph depicting hindlimb placing scores of affected (left) limbs of High dose OP-1-treated animals (10 $\mu$g/intracisternal injection; total OP-1 delivered in 2 injections=20 $\mu$g/animal; N=9 animals; solid squares), Low dose OP-1-treated animals (1 $\mu$g/intracisternal injection; total OP-1 delivered in 2 injections=2 $\mu$g/animal; N=8 animals; open squares), and vehicle-treated animals (N=9, open circles)
Figure 7:
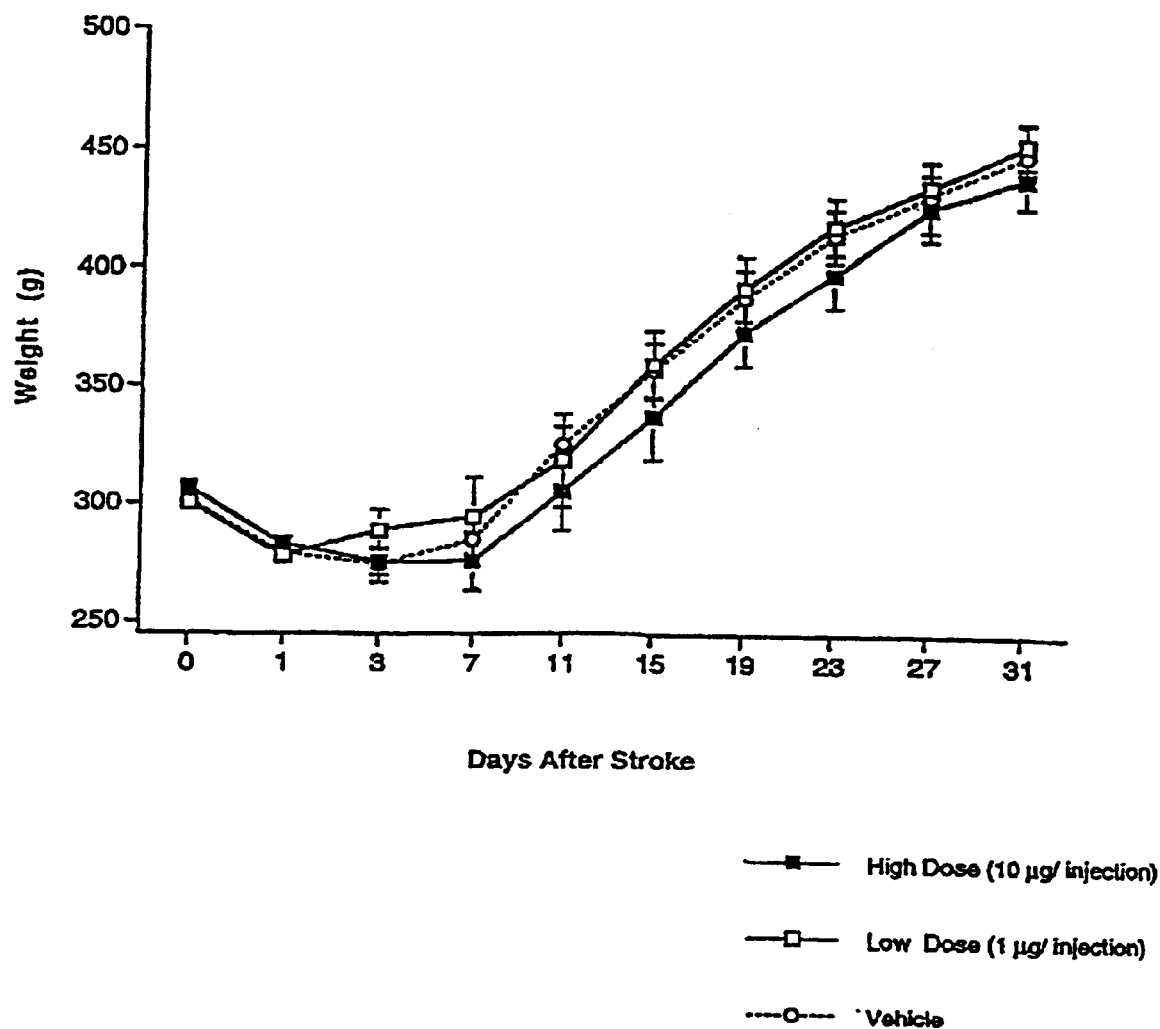
FIG. 7 is a line graph depicting body-weight of High dose OP-1-treated animals (10 $\mu$g/intracisternal injection; total OP-1 delivered in 2 injections=20 $\mu$g/animal; N=9 animals; solid squares), Low dose OP-1-treated animals (1 $\mu$g/intracisternal injection; total OP-1 delivered=2 $\mu$g in 2 injections/animal; N=8 animals; open squares), and vehicle-treated animals (N=9, open circles)
Figure 8A:
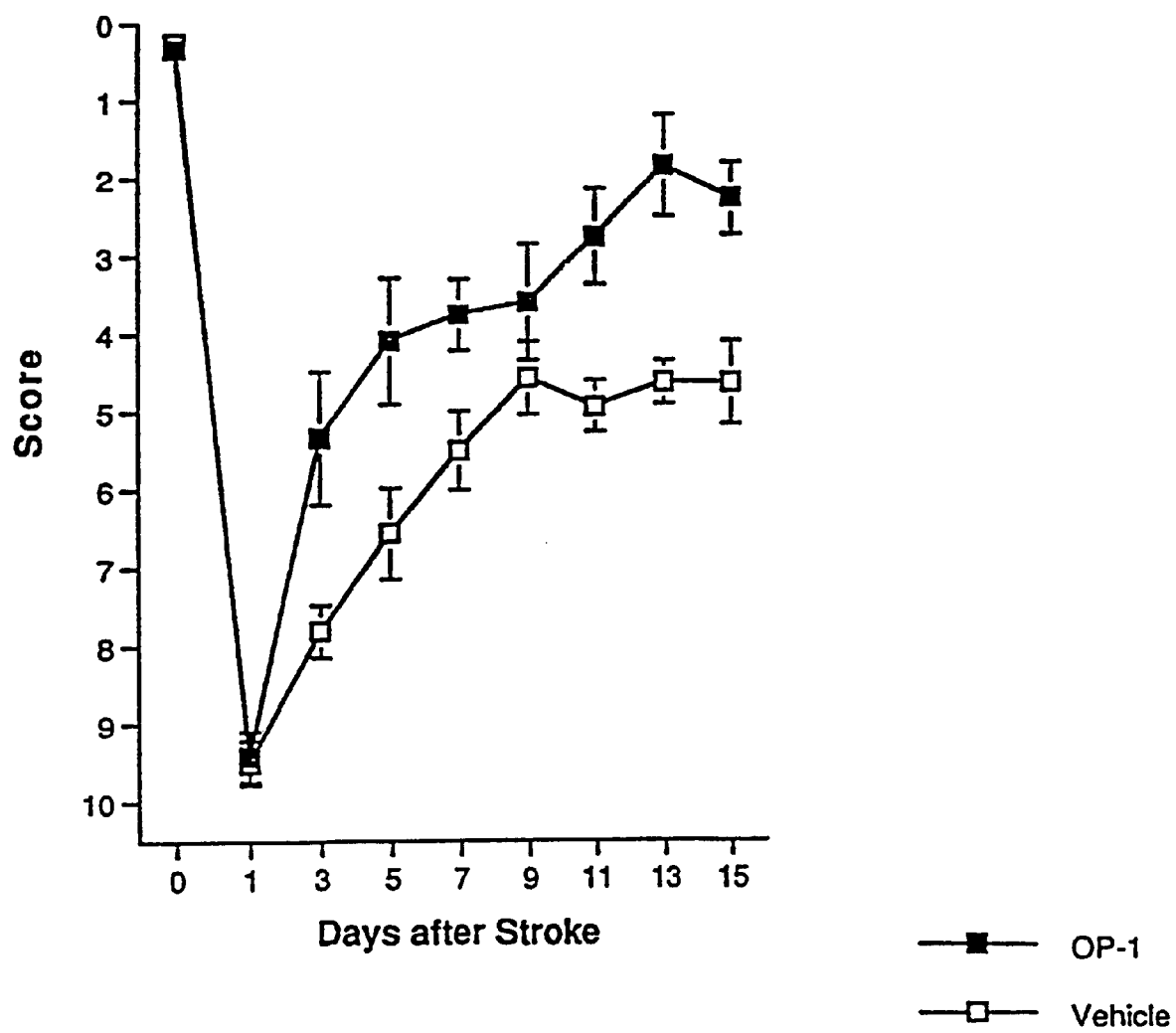
FIGS. 8A–8B are line graphs depicting forelimb placing scores without (8A) and with whisker placing (8B) of affected (left) limbs of OP-1-treated animals (10 $\mu$g/intracisternal injection; N=6 animals; solid squares) and vehicle-treated animals (N=8, open squares)
Figure 8B:
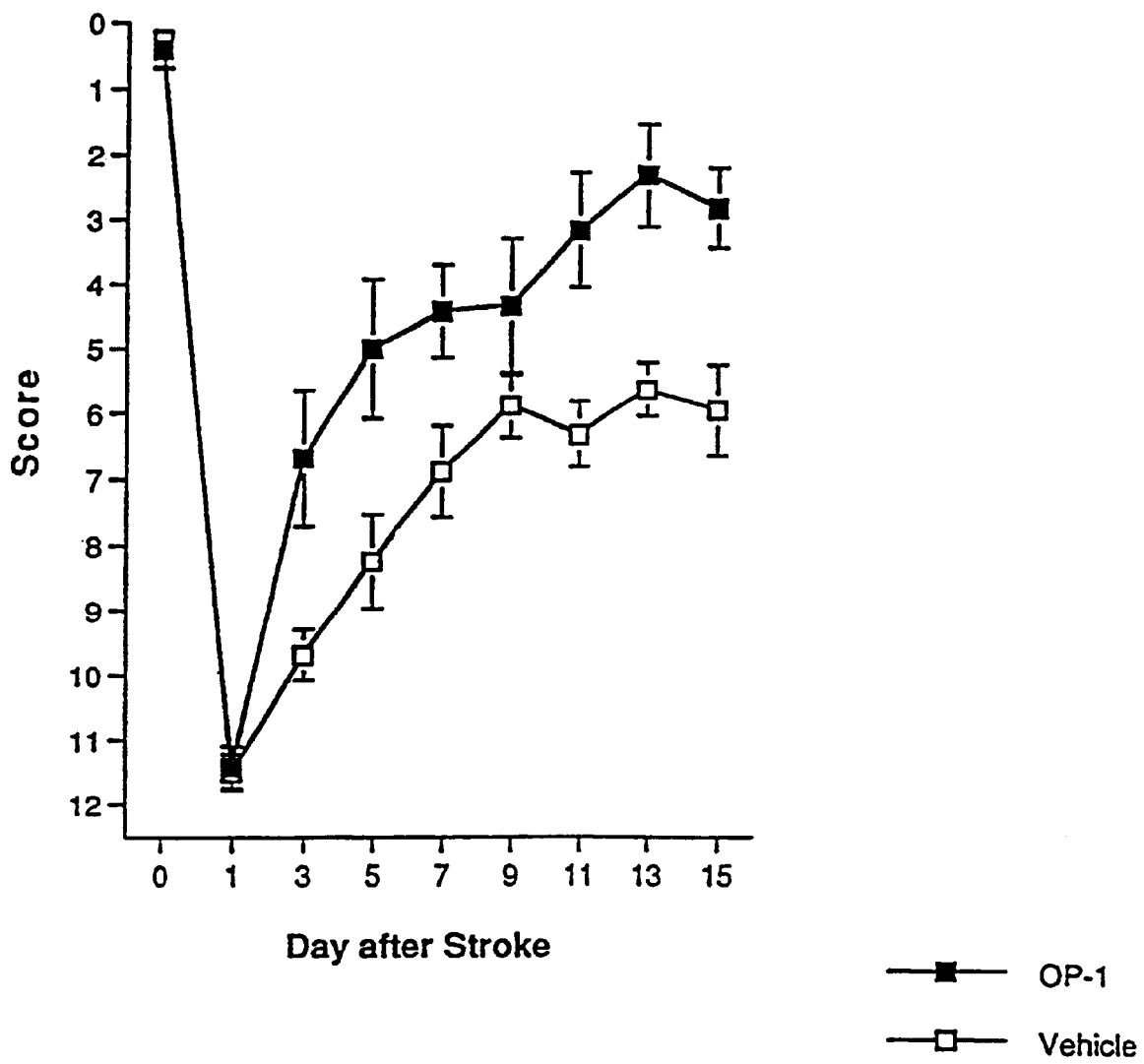
Figure 9:
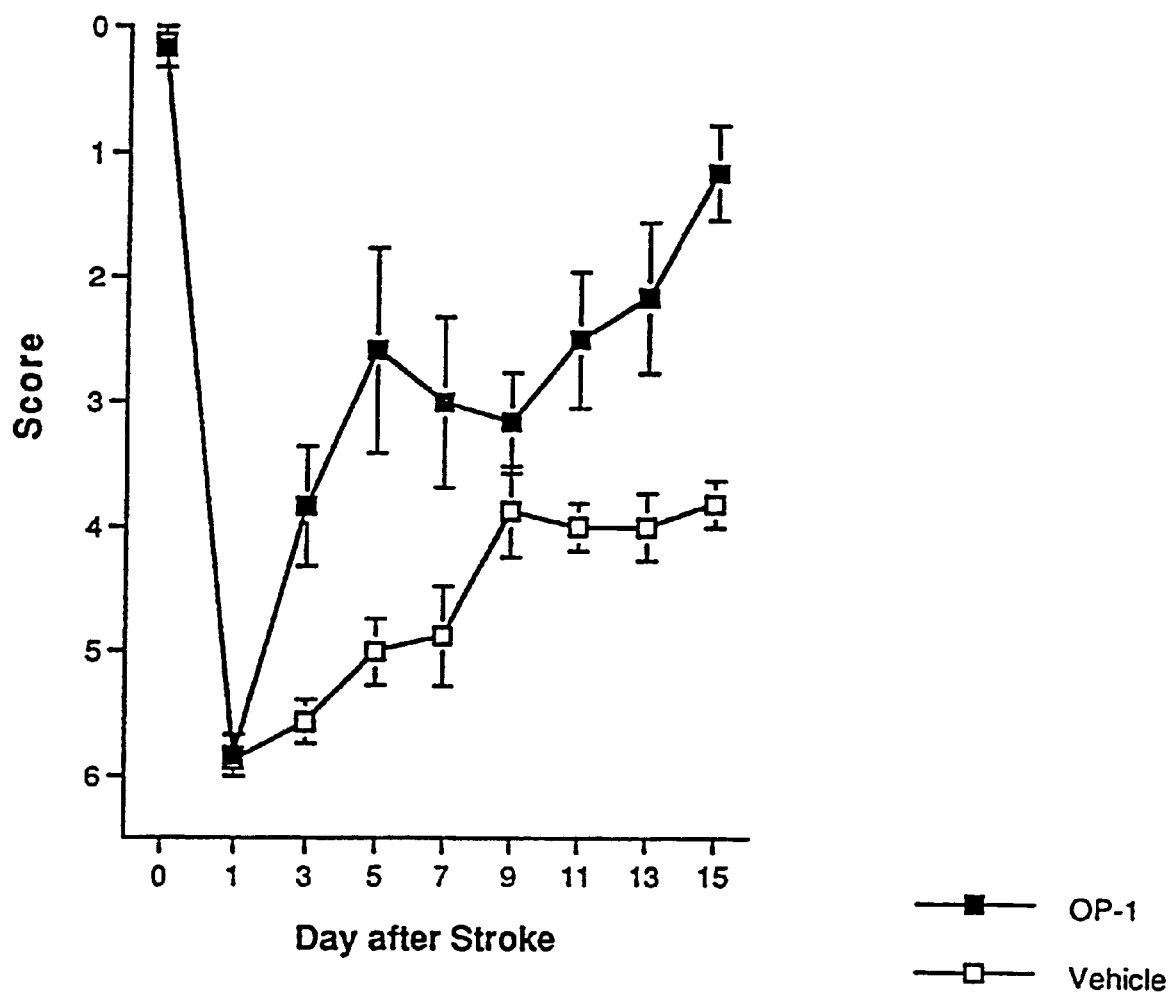
FIG. 9 is a line graph depicting hindlimb placing scores of affected (left) limbs of affected (left) limbs of OP-1-treated animals (10 $\mu$g/intracisternal injection; N=6 animals; solid squares) and vehicle-treated animals (N=8, open squares)
Figure 10:
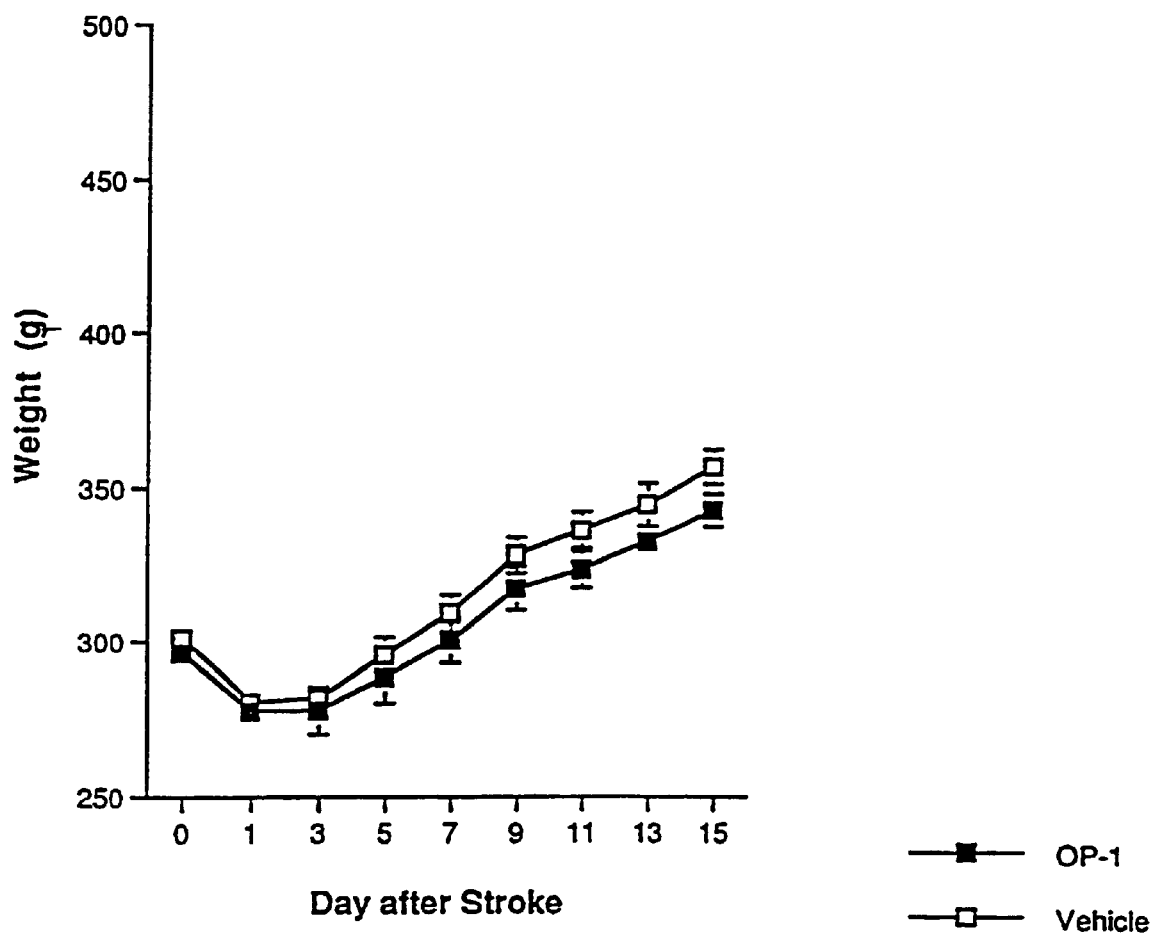
FIG. 10 is a line graph depicting body-weight of OP-1-treated animals (10 $\mu$g/intracisternal injection; N=6 animals; solid squares) and vehicle-treated animals (N=8, open squares).

The time course of body weight during the month after infarction of vehicle-treated animals did not differ significantly from: (a) animals treated with a series (8×10 µg/animal) of OP-1 administrations (FIG. 4; F=0.56, p-n.s.); (b) animals treated with two injections (High dose=2×10 µg/animal; Low dose=2×1 µg/animal) of OP-1 (FIG. 7; F=0.417, p-n.s.); and (c) animals treated with a single injection (10 µg/animal) of OP-1 (FIG. 10; F=0.693, p-n.s.).

Functional Performance of OP-1-Treated Animals and Vehicle-Treated Animals

Following infarction, all animals showed severe disturbances of sensorimotor and reflex function on all four behavioral tests. For the limb placing tests, deficits were confined to the contralateral (left) limbs. Animals receiving the vehicle showed partial recovery on all four behavioral tests during the first month after stroke (see FIGS. 2A–2B, 3A–3B, 5A–5B, 6, 8A–8B, and 9).

(i) Animals Receiving Biweekly OP-1 Administrations

Animals receiving biweekly OP-1 administrations (8×10 µg /injection) recovered more rapidly and to a greater degree than vehicle-treated rats. Improved recovery of OP-1 vs. vehicle-treated animals was most pronounced for the forelimb (FIG. 2A; F=109.0, p=0.0001) and hindlimb placing tasks (FIG. 2B; F=34.8, p=0.0001), and less pronounced, although still significant, for the beam balance (FIG. 3A; F=11.7, p=0.0051). However, there was no significance among the two groups in the postural reflex tests (FIG. 3B; F=3.7, p-n.s.). Enhanced recovery was seen on all subtests of the limb placing tests (visual, tactile, and proprioceptive) following OP-1 treatment (data not shown).

Enhancement of recovery by OP-1 was most pronounced on tests of sensorimotor function of the affected limbs and less pronounced on tests of reflex and postural function. The MCA infarcts did not completely damage forelimb and hindlimb cortical areas, which is compatible with recovery on limb placing tests following focal infarction in the MCA territory.

(ii) Animals Receiving Two OP-1 Administrations

Animals receiving two OP-1 administrations (on post-stroke days 1 and 4) recovered more rapidly and to a greater degree than vehicle-treated rats during the month of behavioral testing. OP-1 (2×1 or 10 µg /injection) induced significant enhancement of recovery of: (a) forelimb placing without whisker (FIG. 5A; F=31.835, p=0.0001; High dose vs. vehicle, p<0.0001; Low dose vs. vehicle, p<0.0001); (b) forelimb placing with whisker (FIG. 5B; F=27.462, p=0.0001; High dose vs. vehicle, p<0.0001; Low dose vs. vehicle, p<0.0001); and (c) hindlimb placing (FIG. 6; F=14.867, p=0.0001; High dose vs. vehicle, p<0.0001; Low dose vs. vehicle, p=0.0036). Although the High dose produced a trend toward better recovery than the Low dose in all three behavioral tests, the differences between the two OP-1-treated groups were non-significant.

(iii) Animals Receiving a Single OP-1 Administrations

Long-term enhancements of functional recovery also were seen with a single administration of OP-1. Animals receiving 10 µg of OP-1 intracisternally 24 hours after the occlusion of the MCA recovered more rapidly and to a greater degree during the month of behavioral testing than vehicle-reated rats. OP-1 induced significant enhancement of recovery of: (a) forelimb placing without whisker (FIG. 8A; F=10.853, p=0.0064); (b) forelimb placing with whisker (FIG. 8B; F=10.629, p=0.0068); and (c) hindlimb placing (FIG. 9; F=15.343, p=0.002).

In the present invention, treatment of an ischemic injury of the central nervous system with OP-1 enhanced both the rate and degree of functional recovery during the first month after infarction. A single administration of an effective dose of OP-1 was sufficient to induce long-term enhancement of functional recovery.

Improved behavioral recovery was seen without a change (e.g., without a decrease) in infarct volume in OP-1-treated compared to vehicle-treated animals. In all these groups, the OP-1 administration commenced one day after ischemia, beyond the apparent "therapeutic window" during which OP-1, according to the teachings of WO 93/04692 and/or WO 94/03200, can reduce infarct size. The current findings are among the first demonstrations that an exogenously administered, biologically active factor can enhance behavioral recovery without a reduction in infarct size in an animal model of stroke.

Similar routine modifications can be made in other accepted models of stroke or traumatic central nervous system injury, to confirm efficacy of morphogen treatment to restore impaired or lost CNS function.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

---

What is claimed is:

1. A method for enhancing recovery of central nervous system function in a mammal, comprising the step of:
   administering an effective amount of a morphogen to a mammal afflicted with a central nervous system injury selected from ischemia and trauma, wherein said morphogen comprises a dimeric protein having the property of inducing tissue-specific morphogenesis in said mammal and comprising a pair of folded polypeptides, each having an amino acid sequence having at least 70% homology with the C-terminal seven-cysteine domain of human OP-1, residues 330–431 of SEQ ID NO:5, wherein said morphogen is not transforming growth factor beta (TGF-β);
   wherein the effective amount of the morphogen is first administered at least 12 hours after the onset of said injury; and wherein the administration enhances the recovery of central nervous system function in the mammal.

2. The method of claim 1 wherein said recovery comprises an improvement in a central nervous system function selected from motor coordination function, sensory perception and speech.

3. The method of claim 2, wherein said sensory perception is selected from vision, hearing, touch, taste, proprioception, and olfaction.

4. The method of claim 1, wherein said mammal is a human.

5. The method of claim 1, wherein the effective amount of a morphogen is provided in a single administration.

6. The method of claim 1, wherein the effective amount of a morphogen is provided in a plurality of administrations.

7. The method of claim 6, wherein the effective amount of a morphogen is provided in two administrations.

8. The method of claim 1, 5, 6 or 7 wherein the effective amount of a morphogen is administered at least 24 hours after the onset of said injury.

9. The method of claim 1, 5, 6 or 7 wherein the effective amount of a morphogen is administered at least 48 hours after the onset of said injury.

10. The method of claim 6, wherein the morphogen is administered daily.

11. The method of claim 6, wherein the morphogen is provided biweekly.

12. The method of claim 6, wherein the morphogen is provided weekly.

13. The method of claim 1, wherein said amino acid sequence is a sequence having greater than 60% amino acid sequence identity with the C-terminal seven-cysteine domain of human OP-1, residues 330–431 of SEQ ID NO:5.

14. The method of claim 1, wherein said amino acid sequence is that of the C-terminal seven-cysteine domain of human OP-1, residues 330–431 of SEQ ID NO:5 or a conservative substitution variant thereof.

15. The method of claim 1, wherein said amino acid sequence is that of the C-terminal seven-cysteine domain of human OP-1, residues 330–431 of SEQ ID NO:5 or a naturally-occurring variant thereof.

16. The method of claim 1, wherein said recovery comprises an improvement in motor function.

17. The method of claim 16, wherein said motor function is selected from posture, balance, grasp and gait.

18. The method of claim 1, wherein said morphogen comprises the amino acid sequence of SEQ ID NO:5.

19. A method for enhancing recovery of central nervous system function in a mammal, comprising the step of:
   administering an effective amount of a morphogen to a mammal afflicted with a central nervous system injury selected from ischemia and trauma, wherein said morphogen comprises a dimeric protein having the property of inducing tissue-specific morphogenesis in said mammal and comprising a pair of folded polypeptides, each having an amino acid sequence selected from the group consisting of:
   (a) Generic Sequence 7 defined by SEQ ID NO:1;
   (b) Generic Sequence 8 defined by SEQ ID NO:2;
   (c) Generic Sequence 9 defined by SEQ ID NO:6; and
   (d) Generic Sequence 10 defined by SEQ ID NO:7,
   wherein said morphogen is not TGF-β;
   wherein the effective amount of the morphogen is first administered at least 12 hours after the onset of said injury; and
   wherein the administration enhances the recovery of central nervous system function in the mammal.

20. The method of claim 19, wherein said morphogen comprises the amino acid sequence of SEQ ID NO:5.

21. A method for enhancing recovery of central nervous system function in a mammal, comprising the step of:
   administering an effective amount of a morphogen to a mammal afflicted with a central nervous system injury selected from ischemia and trauma, wherein said morphogen is selected from the group consisting of human OP-1, mouse OP-1, human OP-2, mouse OP-2, 60A, GDF-1, BMP2A, BMP2B, DPP, Vgl , Vgr-1, BMP3, BMP5, and BMP6;

wherein the effective amount of morphogen is first administered at least 12 hours after the onset of said injury; and wherein the administration enhances the recovery of central nervous system function in the mammal.

22. The method of claim 21, wherein said morphogen comprises the amino acid sequence of SEQ ID NO:5.

23. A method for enhancing recovery of central nervous system function in a mammal, comprising the step of:

administering an effective amount of a morphogen to a mammal afflicted with a central nervous system injury selected from ischemia and trauma, wherein said morphogen is a conservative substitution variant of a morphogen selected from the group consisting of human OP-1, mouse OP-1, human OP-2, mouse OP-2, 60A, GDF-1, BMP2A, BMP2B, DPP, Vgl , Vgr-1, BMP3, BMP5, and BMP6 wherein said morphogen is not TGF-β;

wherein the effective amount of morphogen is first administered at least 12 hours after the onset of said injury; and wherein the administration enhances the recovery of central nervous system function in the mammal.

24. The method of claim 1, 5, 6, 7, 19, 21 or 23 wherein said morphogen is complexed with at least one pro-domain peptide comprising an N-terminal 18 amino acid peptide selected from the group consisting of N-termini of the pro domains of OP-1, OP-2, 60A, GDF-1, BMP-2A, BMP-2B, DPP, Vgl , Vgr-1, BMP-3, BMP-5, and BMP-6.

25. The method of claim 1, 5, 6, 7, 19, 21 or 23 wherein said morphogen is complexed with at least one pro-domain polypeptide that is a conservative substitution variant of a pro-domain polypeptide selected from the group consisting of the pro-domains of OP-1, OP-2, 60A, GDF-1, BMP-2A, BMP-2B, DPP, Vgl , Vgr-1, BMP-3, BMP-5, and BMP-6.

26. The method of claim 1, 5, 6, 7, 19, 21 or 23 wherein said morphogen is noncovalently complexed with at least one solubility-enhancing fragment of a pro-domain polypeptide selected from the pro-domains of naturally-occurring morphogens.

27. The method of claim 26, wherein said morphogen is complexed with a pair of said fragments.

28. The method of claim 1, 5, 6, 7, 19, 21 or 23 wherein said morphogen is obtained from culture supernatant of a morphogen secreting host cell.

29. The method of claim 1, 5, 6, 7, 19, 21 or 23 wherein said morphogen is administered intracisternally, intraventricularly, intrathecally or intravenously.

30. The method of claim 23, wherein said morphogen comprises the amino acid sequence of SEQ ID NO:5.

* * * * *

UNITED STATES PATENT AND TRADEMARK OFFICE
CERTIFICATE OF CORRECTION

PATENT NO. : 6,407,060 B1
DATED : June 18, 2002
INVENTOR(S) : Charette et al.

It is certified that error appears in the above-identified patent and that said Letters Patent is hereby corrected as shown below:

<u>Title page,</u>
Item [73], Assignee, add -- The General Hospital Corporation, Boston, Massachusetts --

Signed and Sealed this

Nineteenth Day of November, 2002

Attest:

Attesting Officer

JAMES E. ROGAN
*Director of the United States Patent and Trademark Office*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 97 amino acids
      (B) TYPE: amino acid (C) STRANDEDNESS:
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= Generic-Seq-7
            /note= "wherein each Xaa is independently selected
            from a group of one or more specified amino acids as
            defined in the specification."

(xi) SEQUENCE DESCRIPTION: SEQ ID NO:1:

Leu Xaa Xaa Xaa Phe Xaa Xaa Xaa Gly Trp Xaa Xaa Xaa Xaa Xaa
1               5                   10                  15

Pro Xaa Xaa Xaa Ala Xaa Tyr Cys Xaa Gly Xaa Cys Xaa Pro
            20              25              30

Xaa Xaa Xaa Xaa Xaa Xaa Xaa Xaa Asn His Ala Xaa Xaa Xaa Xaa Xaa
            35                  40                  45

Xaa Xaa Xaa Xaa Xaa Xaa Xaa Xaa Xaa Xaa Xaa Cys Cys Xaa Pro
        50                  55                  60

Xaa Xaa Xaa Xaa Xaa Xaa Xaa Xaa Leu Xaa Xaa Xaa Xaa Xaa Xaa
65                  70                  75                  80

Val Xaa Leu Xaa Xaa Xaa Xaa Xaa Met Xaa Val Xaa Xaa Cys Xaa Cys
            85                  90                  95

Xaa (2) INFORMATION FOR SEQ ID NO:2:

(i) SEQUENCE CHARACTERISTICS:
        (A) LENGTH: 102 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= Generic-Seq-8
            /note= "wherein each Xaa is independently selected f
            rom a group of one or more specified amino acids as
            defined in the specification."

(xi) SEQUENCE DESCRIPTION: SEQ ID NO:2:

Cys Xaa Xaa Xaa Xaa Leu Xaa Xaa Xaa Phe Xaa Xaa Xaa Gly Trp Xaa
1               5                   10                  15

Xaa Xaa Xaa Xaa Xaa Pro Xaa Xaa Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
        35                  40                  45

Xaa Xaa Xaa Xaa Xaa Xaa Xaa Xaa Xaa Xaa Xaa Xaa Xaa Xaa Xaa
        50                  55                  60

Xaa Cys Cys Xaa Pro Xaa Xaa Xaa Xaa Xaa Xaa Xaa Leu Xaa Xaa
65                  70                  75                  80

Xaa Xaa Xaa Xaa Xaa Val Xaa Leu Xaa Xaa Xaa Xaa Xaa Met Xaa Val
            85                  90                  95

Xaa Xaa Cys Xaa Cys Xaa
            100

(2) INFORMATION FOR SEQ ID NO:3:

(i) SEQUENCE CHARACTERISTICS:
            (A) LENGTH: 102 amino acids
            (B) TYPE: amino acid
            (C) STRANDEDNESS:
            (D) TOPOLOGY: linear (ii) MOLECULE TYPE: protein (ix) FEATURE:
            (A) NAME/KEY: Protein
            (B) LOCATION: 1..102
            (D) OTHER INFORMATION: /label= OPX
                 /note= "wherein each Xaa is independently selected
                 from a group of one or more specified amino acids as
                 defined in the specification."

(xi) SEQUENCE DESCRIPTION: SEQ ID NO:3:

```
Cys Xaa Xaa His Glu Leu Tyr Val Xaa Phe Xaa Asp Leu Gly Trp Xaa
1               5                   10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
            35                  40                  45

Ile Xaa Gln Xaa Leu Val His Xaa Xaa Xaa Pro Xaa Xaa Val Pro Lys
    50                  55                  60

Xaa Cys Cys Ala Pro Thr Xaa Leu Xaa Ala Xaa Ser Val Leu Tyr Xaa
65              70                  75                  80

Asp Xaa Ser Xaa Asn Val Xaa Leu Xaa Lys Xaa Arg Asn Met Val Val
            85                  90                  95

Xaa Ala Cys Gly Cys His
            100
```

(2) INFORMATION FOR SEQ ID NO:4:

(i) SEQUENCE CHARACTERISTICS:
            (A) LENGTH: 1822 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: HOMO SAPIENS
            (F) TISSUE TYPE: HIPPOCAMPUS (ix) FEATURE:
            (A) NAME/KEY: CDS
            (B) LOCATION: 49..1341
            (C) IDENTIFICATION METHOD: experimental
            (D) OTHER INFORMATION: /function= "OSTEOGENIC PROTEIN"
                 /product= "OP1"
                 /evidence= EXPERIMENTAL
                 /standard_name= "OP1"

(xi) SEQUENCE DESCRIPTION: SEQ ID NO:4:

```
GGTGCGGGCC CGGAGCCCGG AGCCCGGGTA GCGCGTAGAG CCGGCGCG ATG CAC GTG        57
                                                    Met His Val
                                                      1

CGC TCA CTG CGA GCT GCG GCG CCG CAC AGC TTC GTG GCG CTC TGG GCA        105
Arg Ser Leu Arg Ala Ala Ala Pro His Ser Phe Val Ala Leu Trp Ala
      5                  10                  15

CCC CTG TTC CTG CTG CGC TCC GCC CTG GCC GAC TTC AGC CTG GAC AAC        153
Pro Leu Phe Leu Leu Arg Ser Ala Leu Ala Asp Phe Ser Leu Asp Asn
 20                  25                  30                  35

GAG GTG CAC TCG AGC TTC ATC CAC CGG CGC CTC CGC AGC CAG GAG CGG        201
```

-continued

```
Glu Val His Ser Ser Phe Ile His Arg Arg Leu Arg Ser Gln Glu Arg
             40                  45                  50

CGG GAG ATG CAG CGC GAG ATC CTC TCC ATT TTG GGC TTG CCC CAC CGC      249
Arg Glu Met Gln Arg Glu Ile Leu Ser Ile Leu Gly Leu Pro His Arg
             55                  60                  65

CCG CGC CCG CAC CTC CAG GGC AAG CAC AAC TCG GCA CCC ATG TTC ATG      297
Pro Arg Pro His Leu Gln Gly Lys His Asn Ser Ala Pro Met Phe Met
         70                  75                  80

CTG GAC CTG TAC AAC GCC ATG GCG GTG GAG GAG GGC GGC GGG CCC GGC      345
Leu Asp Leu Tyr Asn Ala Met Ala Val Glu Glu Gly Gly Gly Pro Gly
     85                  90                  95

GGC CAG GGC TTC TCC TAC CCC TAC AAG GCC GTC TTC AGT ACC CAG GGC      393
Gly Gln Gly Phe Ser Tyr Pro Tyr Lys Ala Val Phe Ser Thr Gln Gly
100                 105                 110                 115

CCC CCT CTG GCC AGC CTG CAA GAT AGC CAT TTC CTC ACC GAC GCC GAC      441
Pro Pro Leu Ala Ser Leu Gln Asp Ser His Phe Leu Thr Asp Ala Asp
                120                 125                 130

ATG GTC ATG AGC TTC GTC AAC CTC GTG GAA CAT GAC AAG GAA TTC TTC      489
Met Val Met Ser Phe Val Asn Leu Val Glu His Asp Lys Glu Phe Phe
            135                 140                 145

CAC CCA CGC TAC CAC CAT CGA GAG TTC CGG TTT GAT CTT TCC AAG ATC      537
His Pro Arg Tyr His His Arg Glu Phe Arg Phe Asp Leu Ser Lys Ile
        150                 155                 160

CCA GAA GGG GAA GCT GTC ACG GCA GCC GAA TTC CGG ATC TAC AAG GAC      585
Pro Glu Gly Glu Ala Val Thr Ala Ala Glu Phe Arg Ile Tyr Lys Asp
    165                 170                 175

TAC ATC CGG GAA CGC TTC GAC AAT GAG ACG TTC CGG ATC AGC GTT TAT      633
Tyr Ile Arg Glu Arg Phe Asp Asn Glu Thr Phe Arg Ile Ser Val Tyr
180                 185                 190                 195

CAG GTG CTC CAG GAG CAC TTG GGC AGG GAA TCG GAT CTC TTC CTG CTC      681
Gln Val Leu Gln Glu His Leu Gly Arg Glu Ser Asp Leu Phe Leu Leu
                200                 205                 210

GAC AGC CGT ACC CTC TGG GCC TCG GAG GAG GGC TGG CTG GTG TTT GAC      729
Asp Ser Arg Thr Leu Trp Ala Ser Glu Glu Gly Trp Leu Val Phe Asp
            215                 220                 225

ATC ACA GCC ACC AGC AAC CAC TGG GTG GTC AAT CCG CGG CAC AAC CTG      777
Ile Thr Ala Thr Ser Asn His Trp Val Val Asn Pro Arg His Asn Leu
        230                 235                 240

GGC CTG CAG CTC TCG GTG GAG ACG CTG GAT GGG CAG AGC ATC AAC CCC      825
Gly Leu Gln Leu Ser Val Glu Thr Leu Asp Gly Gln Ser Ile Asn Pro
    245                 250                 255

AAG TTG GCG GGC CTG ATT GGG CGG CAC GGG CCC CAG AAC AAG CAG CCC      873
Lys Leu Ala Gly Leu Ile Gly Arg His Gly Pro Gln Asn Lys Gln Pro
260                 265                 270                 275

TTC ATG GTG GCT TTC TTC AAG GCC ACG GAG GTC CAC TTC CGC AGC ATC      921
Phe Met Val Ala Phe Phe Lys Ala Thr Glu Val His Phe Arg Ser Ile
                280                 285                 290

CGG TCC ACG GGG AGC AAA CAG CGC AGC CAG AAC CGC TCC AAG ACG CCC      969
Arg Ser Thr Gly Ser Lys Gln Arg Ser Gln Asn Arg Ser Lys Thr Pro
            295                 300                 305

AAG AAC CAG GAA GCC CTG CGG ATG GCC AAC GTG GCA GAG AAC AGC AGC     1017
Lys Asn Gln Glu Ala Leu Arg Met Ala Asn Val Ala Glu Asn Ser Ser
        310                 315                 320

AGC GAC CAG AGG CAG GCC TGT AAG AAG CAC GAG CTG TAT GTC AGC TTC     1065
Ser Asp Gln Arg Gln Ala Cys Lys Lys His Glu Leu Tyr Val Ser Phe
    325                 330                 335

CGA GAC CTG GGC TGG CAG GAC TGG ATC ATC GCG CCT GAA GGC TAC GCC     1113
Arg Asp Leu Gly Trp Gln Asp Trp Ile Ile Ala Pro Glu Gly Tyr Ala
340                 345                 350                 355
```

```
GCC TAC TAC TGT GAG GGG GAG TGT GCC TTC CCT CTG AAC TCC TAC ATG      1161
Ala Tyr Tyr Cys Glu Gly Glu Cys Ala Phe Pro Leu Asn Ser Tyr Met
            360                 365                 370

AAC GCC ACC AAC CAC GCC ATC GTG CAG ACG CTG GTC CAC TTC ATC AAC      1209
Asn Ala Thr Asn His Ala Ile Val Gln Thr Leu Val His Phe Ile Asn
        375                 380                 385

CCG GAA ACG GTG CCC AAG CCC TGC TGT GCG CCC ACG CAG CTC AAT GCC      1257
Pro Glu Thr Val Pro Lys Pro Cys Cys Ala Pro Thr Gln Leu Asn Ala
    390                 395                 400

ATC TCC GTC CTC TAC TTC GAT GAC AGC TCC AAC GTC ATC CTG AAG AAA      1305
Ile Ser Val Leu Tyr Phe Asp Asp Ser Ser Asn Val Ile Leu Lys Lys
405                 410                 415

TAC AGA AAC ATG GTG GTC CGG GCC TGT GGC TGC CAC TAGCTCCTCC           1351
Tyr Arg Asn Met Val Val Arg Ala Cys Gly Cys His
420                 425                 430

GAGAATTCAG ACCCTTTGGG GCCAAGTTTT TCTGGATCCT CCATTGCTCG CCTTGGCCAG    1411

GAACCAGCAG ACCAACTGCC TTTTGTGAGA CCTTCCCCTC CCTATCCCCA ACTTTAAAGG    1471

TGTGAGAGTA TTAGGAAACA TGAGCAGCAT ATGGCTTTTG ATCAGTTTTT CAGTGGCAGC    1531

ATCCAATGAA CAAGATCCTA CAAGCTGTGC AGGCAAAACC TAGCAGGAAA AAAAAACAAC    1591

GCATAAAGAA AAATGGCCGG GCCAGGTCAT TGGCTGGGAA GTCTCAGCCA TGCACGGACT    1651

CGTTTCCAGA GGTAATTATG AGCGCCTACC AGCCAGGCCA CCCAGCCGTG GGAGGAAGGG    1711

GGCGTGGCAA GGGGTGGGCA CATTGGTGTC TGTGCGAAAG GAAAATTGAC CCGGAAGTTC    1771

CTGTAATAAA TGTCACAATA AAACGAATGA ATGAAAAAAA AAAAAAAAA A              1822

(2) INFORMATION FOR SEQ ID NO:5:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:5:

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
```

```
                       165                 170                 175
Tyr Lys Asp Tyr Ile Arg Glu Arg Phe Asp Asn Glu Thr Phe Arg Ile
                    180                 185                 190

Ser Val Tyr Gln Val Leu Gln Glu His Leu Gly Arg Glu Ser Asp Leu
                195                 200                 205

Phe Leu Leu Asp Ser Arg Thr Leu Trp Ala Ser Glu Glu Gly Trp Leu
            210                 215                 220

Val Phe Asp Ile Thr Ala Thr Ser Asn His Trp Val Asn Pro Arg
225                 230                 235                 240

His Asn Leu Gly Leu Gln Leu Ser Val Glu Thr Leu Asp Gly Gln Ser
                    245                 250                 255

Ile Asn Pro Lys Leu Ala Gly Leu Ile Gly Arg His Gly Pro Gln Asn
                260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                    325                 330                 335

Val Ser Phe Arg Asp Leu Gly Trp Gln Asp Trp Ile Ile Ala Pro Glu
                340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
        370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                    405                 410                 415

Leu Lys Lys Tyr Arg Asn Met Val Val Arg Ala Cys Gly Cys His
                420                 425                 430

(2) INFORMATION FOR SEQ ID NO:6:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= Generic-Seq-9
            /note= "wherein each Xaa is independently selected
            from a group of one or more specified amino acids
            as defined in the
            specification."

(xi) SEQUENCE DESCRIPTION: SEQ ID NO:6:

Xaa Xaa Xaa Xaa Xaa Xaa Xaa Xaa Xaa Xaa Xaa Xaa Xaa Xaa Xaa Xaa
1               5                   10                  15

Pro Xaa Xaa Xaa Xaa Xaa Xaa Xaa Cys Xaa Gly Xaa Cys Xaa Xaa Xaa
                20                  25                  30

Xaa Xaa Xaa Xaa Xaa Xaa Xaa Xaa Xaa Xaa Xaa Xaa Xaa Xaa Xaa
```

```
                  35                  40                  45
Xaa Xaa Xaa Xaa Xaa Xaa Xaa Xaa Xaa Xaa Xaa Xaa Cys Xaa Pro
 50                  55                  60

Xaa Xaa Xaa Xaa Xaa Xaa Xaa Xaa Leu Xaa Xaa Xaa Xaa Xaa Xaa
 65                  70                  75                  80

Xaa Xaa Xaa Xaa Xaa Xaa Xaa Xaa Xaa Xaa Xaa Xaa Cys Xaa Cys
                     85                  90                  95

Xaa
```

(2) INFORMATION FOR SEQ ID NO:7:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= Generic-Seq-10
           /note= "wherein each Xaa is independently selected
           from a group of one or more specified amino acids as
           defined in the specification."

(xi) SEQUENCE DESCRIPTION: SEQ ID NO:7:

```
Cys Xaa Xaa Xaa Xaa Xaa Xaa Xaa Xaa Xaa Xaa Xaa Xaa Xaa Xaa
 1                   5                  10                  15

Xaa Xaa Xaa Xaa Xaa Pro Xaa Xaa Xaa Xaa Xaa Xaa Cys Xaa Gly
                 20                  25                  30

Xaa Cys Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
 50                  55                  60

Xaa Xaa Cys Xaa Pro Xaa Xaa Xaa Xaa Xaa Xaa Xaa Leu Xaa Xaa
 65                  70                  75                  80

Xaa Xaa Xaa Xaa Xaa Xaa Xaa Xaa Xaa Xaa Xaa Xaa Xaa Xaa Xaa
                     85                  90                  95

Xaa Xaa Cys Xaa Cys Xaa
                100
```

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Protein
        (B) LOCATION: 1..5
        (D) OTHER INFORMATION: /note= "wherein each Xaa is
           independently selected from a group of one or more
           specified amino acids as defined in the specification"

(xi) SEQUENCE DESCRIPTION: SEQ ID NO:8:

```
Cys Xaa Xaa Xaa Xaa
 1                5
```

```
-continued (2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Protein
        (B) LOCATION: 1..5
        (D) OTHER INFORMATION: /note= "wherein each Xaa is
            independently selected from a group of one or more
            specified amino acids as defined in the specification"

(xi) SEQUENCE DESCRIPTION: SEQ ID NO:9:

Cys Xaa Xaa Xaa Xaa
1               5
```